United States Patent
Wadoux et al.

(10) Patent No.: US 6,190,707 B1
(45) Date of Patent: Feb. 20, 2001

(54) COLD-SENSITIVE BREAD-MAKING YEASTS

(75) Inventors: Isabelle Wadoux, Marco-En-Baroeul; Didier Colavizza, Conde-sur-l'Escaut; Annie Loiez, Lille, all of (FR)

(73) Assignee: Lesaffre et Cie, Paris (FR)

( * ) Notice: Under 35 U.S.C. 154(b), the term of this patent shall be extended for 0 days.

(21) Appl. No.: 09/125,028

(22) PCT Filed: Feb. 7, 1997

(86) PCT No.: PCT/FR97/00254
§ 371 Date: Aug. 7, 1998
§ 102(e) Date: Aug. 7, 1998

(87) PCT Pub. No.: WO97/28693
PCT Pub. Date: Aug. 14, 1997

(30) Foreign Application Priority Data

Feb. 8, 1996 (FR) ................................................. 96 01562

(51) Int. Cl.[7] ............................. C12N 1/18; C12N 1/19; A21D 8/04; A21D 10/00
(52) U.S. Cl. ................................. 426/19; 426/27; 426/62; 426/549; 435/254.21; 435/255.2
(58) Field of Search ........................... 435/254.11, 254.2, 435/254.21, 255.1, 255.2; 426/19, 61, 62, 549, 27

(56) References Cited

U.S. PATENT DOCUMENTS 5,399,492  3/1995  Gysler et al. .................... 435/172.1
5,480,798  1/1996  Gysler et al. .................... 435/255.2

FOREIGN PATENT DOCUMENTS 0 487 878  6/1992  (EP) .
0 667 099  8/1995  (EP) .

Primary Examiner—Keith D. Hendricks
(74) Attorney, Agent, or Firm—Henderson & Sturm LLP

(57) ABSTRACT

A strain of bread-mixing yeast for use in obtaining fresh bread-making yeasts: giving at least 100 ml in 2 hours at 30° C. in test $A_1$, preferably at least 110 ml., more preferably at least 150 ml; complying with the following ratio:

$$\frac{\text{release of } CO_2 \text{ in 48 hours at } 8° C. \text{ in test } A_1}{\text{release of } CO_2 \text{ in 2 hours at } 30° C. \text{ in test } A_1}$$

less than 45%, preferably less than 40% and even more preferably less than 30%, it being understood that, according to test $A_1$, to 20 g of flour incubated at the temperature chosen for measurement, a weight of compressed yeast is added corresponding to 160 mg of dry matter, this yeast being diluted in 15 ml of water containing 27 g of NaCl per liter and 4 g of $(NH_4)_2SO_4$ per liter; this is mixed with a spatula for 40 seconds, in order to obtain a dough which is placed on a bain-marie set to the chosen temperature; thirteen minutes after the start of mixing; the vessel containing the dough is sealed hermetically; the total quantity of gas produced is measured after 60, then 120 minutes or several hours; this quantity is expressed in ml at 20° C. and at 760 mmHg. A method of using fresh or dry yeasts of the present invention in a process of deferred bread-making. A method of using fresh or dry yeasts of the present invention for the production of fermented doughs in bulk with long prefermentation, which then make it possible to obtain, with a short finishing, aromatic loaves of the French type. A method of using yeasts of the present invention obtaining leavens of bacteria and of yeasts.

46 Claims, 3 Drawing Sheets

CONSTRUCTION OF THE PLASMID pUC9_3162 ΔG 418

SEQUENCE LISTING

```
<160> NUMBER OF SEQ ID NOS: 2

<210> SEQ ID NO 1
<211> LENGTH: 9621
<212> TYPE: DNA
<213> ORGANISM: Saccharomyces cerevisiae
<220> FEATURE:
<221> NAME/KEY: misc_feature
<222> LOCATION: (9318)
<223> OTHER INFORMATION: Use of n signifies any of g, a, c or t

<400> SEQUENCE: 1
tcttggtgta ttatacgcgt ctttggtctg tcaagtcctt ttataagaca gcaaatgtca      60
tttctttcta agtgtagccg gcgtgtattg tttatgactt tttttttctac cgctggcatt     120 aaagtgagag gttcacgatg cgttcccaat aacttcgtag ggatggcgat caatatacaa     180
atagagggaa gccaaactcc ccactataaa gctgttggca cggtttttata agcttcaacc    240 tttctaggct acaggatact caaaaaaaat tactgcggta ttatcaacat agtgctcttt     300
ggaaaaaaaa aaagaatagt actcattaaa gccacctgac tcaagtcttc tattgacggt     360
aataagttag caagcatgga agctatttca caattacgtg gtgttccatt gacacaccaa     420
aaggacttta gctgggtctt tttagtagat tggattctca cggtggtagt atgtttgaca     480
atgatattct acatgggaag aatctatgca taccttgtaa gttttatatt agaatggcta     540
ctatggaaac gagcgaaaat caagataaat gttgagacac ttcgtgtctc cttactaggt     600
ggtcgaatac atttttaaaaa cctttccgta atacacaaag attatacgat ttcggtatta    660
gagggtagtt taacatggaa atactggctt ttaaattgca gaaaagcaga attgatagag     720
aatgacaagt cttcttctgg caaaaaagca aagcttccgt gtaaaatttc cgtagaatgt     780
```

-continued

```
gaaggtctag aaattttat ttacaacaga acagtggcgt acgataatgt tataaactta     840
ctatcaaaag atgaacgcga taaatttgaa aaataccta atgagcattc ttttcctgaa     900
cctttagcg atggaagtag tgctgataaa ttagatgaag atctaagcga atctgcatac     960
acaacgaact ctgatgcatc aattgttaat gacagggact accaagaaac agatatcggc    1020
aaacatccaa agctactgat gtttttacca attgagctta aatttagccg cggttcccta    1080
ctgttaggaa acaaattcac gccatctgtt atgattctaa gttatgaaag tggaaaaggc    1140
ataatagatg ttttacctcc aaaagagcga ttagatttat acagaaataa aacacagatg    1200
gaattcaaaa acttcgaaat ttctatcaaa caaatattg gttacgatga tgctattgga     1260
ttgaagttta aaatagatag agggaaagtg tcaaagttat ggaaaacgtt tgtacgagtc    1320
tttcagatag taaccaagcc tgttgtaccg aaaaagacta aaaaagcgc aggcacatca     1380
gatgacaatt tctatcataa atggaaaggt ttatctcttt ataaggcttc tgcgggcgac    1440
gctaaagcaa gtgatttaga tgatgttgag ttcgatttga cgaaccatga atatgctaaa    1500
tttacatcaa ttttaaaatg cccaaaggtc acaattgcat atgacgtgga tgttccgggc    1560
gttgtgccac atggtgcaca tccgacaata cctgatattg atggaccaga tgtgggcaat    1620
aacggagcac ctccagattt tgctttagat gttcaaattc acgaggatc catctgttac     1680
ggaccttggg ctcaaagaca agtcagtcat ctacaaagag ttctatcacc ggtagtttca    1740
aggacagcca aacctataaa aaaactcccg ccaggttcta aagaatata tacacttttc    1800
aggatgaata tatcaataat ggaagatact acttggcgta taccgacgag ggaaagtagc    1860
aaagaccccg aattttgaa acactacaaa gaaactaatg aagaatatag gccatttgga     1920
tggatggatc tccgattttg taaggacacc tatgcraatt tcaatataag tgttgtcct    1980
acagtgcaag gttttcagaa taatttccat gttcatttcc tggaaaccga aattaggtca    2040
agtgttaatc acgatatttt gttaaaaagc aaggtattcg atattgatgg ggatattgga    2100
tatccattgg gttggaatag caaagctata tggataatta acatgaagtc agaacaatta    2160
gaggcgtttc tgctacgtga gcatataact ttagttgcag atacgctttc agactttcc     2220
gctggtgayc ctacgcctta cgaacttttt agaccattcg tatacaaagt caattgggaa    2280
atggaaggat attcyatcta cttaaacgtc aatgatcaca atattgttaa caatccgtta    2340
gattttaacg aaaactgtta tttatccctt catggtgata agctttcaat tgatgtcacg    2400
gtaccccgtg agagtatttt ggggacatac acagatatgt cctacgagat ctcaactcca    2460
atgttcagaa tgatgttaaa taccccccct tggaatacat tgaacgaatt catgaaacat    2520
aaagaagtgg ggagagcata cgactttaca attaaaggtt cttaccttct ctattctgag    2580
ttagatattg ataatgtcga tacgctagtc atagagtgta acagcaagag tacagtactt    2640
cactgctatg ggtttgtcat gaggtattta acaaacgtaa agatgaatta cttcggtgaa    2700
ttttttaatt ttgtgacgtc agaagagtac acgggtgtcc ttggcgctag ggaagtcgga    2760
gatgtcacta cgaaaagctc ggtggcggat ttggcatcta ctgtagattc agggtaccaa    2820
aatagcagtc taaagaacga atctgaggat aaaggtccta tgaaaaggtc agatttgaaa    2880
aggactacca acgaaactga tatttggttc acattttcgg tttgggatgg tgctctgata    2940
ttaccagaaa cgatttacag ttttgatcca tgcattgcac tacattttgc cgaacttgtc    3000
gtggatttca gaagttgtaa ttattatatg gacataatgg cggttctcaa cgggacttca    3060
ataaagcggc acgtttcaaa acaaataaat gaagtatttg atttttatacg tcgtaataac    3120
```

-continued

```
ggtgctgatg agcaggagca cggattgctt tcggacctca ccattcatgg acatagaatg      3180
tatggattac cacccacaga acctacctac ttttgtcaat gggatatcaa tctcggagat      3240
ttatgcattg attcagatat tgaatttata aagggattct ttaattcctt ttataagata      3300
ggttttggct acaatgactt ggaaaatata ttattatatg acactgagac cattaatgat      3360
atgacctcgc taactgtgca cgttgaaaaa ataagaatag gccttaaaga tccggtgatg      3420
aaatctcaat cagttattag tgctgaatcg atattgttta ctttgatcga ctttgaaaac      3480
gaaaaatatt cacaaagaat agacgtgaaa attccaaaat tgacaatttc gttgaattgc      3540
gtgatgggcg atggcgtaga cacatcattt ctcaaattcg aaacaaaatt aagatttaca      3600
aactttgagc aatacaagga tatcgataaa aaaagatcag aacaacgcag atatataaca      3660
atacacgatt caccctatca tagrtgtcct tttcttcttc cgctgtttta tcaggattcg      3720
gatacatacc aaaacctgta cggggctata gcaccatctt cgtctatccc aactttacct      3780
cttcccactt tgcctgatac tatagattat atcattgaag atattgtggg cgagtatgct      3840
acccttctgg agaccacaaa tccattcaag aacatattcg cagaaactcc atcaactatg      3900
gagccttcaa gagccagctt cagtgaagat gataatgagg aaggagcgga cccttcaagc      3960
ttcaaacctg ttgcttttac agaagacaga aaccacgaaa gggataacta tgttgttgat      4020
gtttcatata ttctgttgga tgtcgacccg ttgcttttta ttttcgctaa gagtttatta      4080
gaacagcttt actctgaaaa catggtacaa gtcttagacg atattgaaat tgggattgtg      4140
aaacgattaa gcaaccttca agaagggatt acttctattt caaacattga tatccatatt      4200
gcttatctaa atttaatttg gcaagagaca ggtgaggaag gttttgagct ctatttagat      4260
cgtattgatt atcaaatgag tgaaaagtct ctagagaaga accgaacaaa taaattatta      4320
gaggtagcag ctttagcaaa ggtaaaaact gtcagagtga ctgttaacca gaagaaaaat      4380
ccagacttgt ctgaagatcg tccccctgca ctgtcgctag ggattgaggg tttcgaagta      4440
tggtcttcta cagaagatag acaagttaac tcattaaact aacgtcatca agatattacc      4500
atagacgaat ctcaaatgga atggctgttt gagtactgta gtgaccaggg aaatcttatt      4560
caagaggttt gcacttcttt taattctatt cagaacacca gaagtaattc aaagacagaa      4620
ctcatttcaa agctcacagc cgcaagcgaa tattatcaaa ttagtcatga tccttacgtc      4680
ataacaaaac ctgcttttat tatgagactt tccaaagggc atgtgcgtga gaatcgtagt      4740
tggaaaatta ttacgcgtct gagacacatt ttaacgtacc ttcctgatga ttggcaaagc      4800
aacatcgacg aagtgctaaa agaaagaaa tatacctctg ctaaagatgc aaaaaatatc      4860
ttcatgtctg tgttttcgac ttggagaaat tgggagttct cagatgttgc aaggtcgtat      4920
atatacggca aattattcac ggcagaaaat gagaaacata aacaaaattt gattaaaaaa      4980
ttgttgaagt gtaccatggg atcatttttac cttactgttt atggtgaggg atatgaggtt      5040
gagcataatt ttgttgttgc ggatgccaat ctggtagtgg atttgacgcc tccggtgaca      5100
agcttacctt caaatcgaga rgagactatt gaaattacgg gaagagtagg ctcagtaaaa      5160
ggaaaattca gtgataggtt acttaaattg caagatctta ttccactcat tgcagcagtg      5220
ggcgaagatg acaaaagtga tccaaaaaag gagttatcaa agcaattcaa aatgaacacc      5280 gtttttattag tggataaaag tgaactgcaa ctggtcatgg accaaacgaa gctgataagt      5340
agaacagttg ggggtagagt tagtttacta tgggaaaatc taaagattc aactagtcaa      5400 gcgggttcat tggttatatt ttcccagaaa tcggaagtgt ggttaaaaca cacatctgtc      5460
attttgggag aagctcaact gcgcgacttt tcaattttag cgactactga ggcatggtca      5520
```

```
cacaagccta cgattctgat aaacaaccag tgcgcagatc ttcattttag agcaatgagt    5580
tcaactgagc aattagtaac cgctattact gaaattaggg aaagtctgat gatgattaaa    5640
gagcgcataa agtttaaacc taaatcaaag aaaaagtccc aatttgtcga ccagaaaatt    5700
aacacagtct tgtcatgtta tttttcaaac gttagttctg aagttatgcc gctctcgcca    5760
ttttatattc gtcacgaagc caagcagctt gatatatatt ttaacaaatt cggttcaaat    5820
gagattttgt taagcatatg ggatactgat tttttcatga catcgcacca gacaaaggag    5880
caatacctaa ggttttcatt tggcgatatt gaaattaaag gaggaatttc tagagaaggc    5940
tattcgttga taaacgttga catctcaata tctatgatta agttaacctt tcggagccg     6000 cgccgtattg taaacagttt tttacaagat gaaaagcttg cttctcaggg tatcaatctg    6060
ttatattccc tgaagccttt attctttagt tcaaatctac caaaaaaaga gaagcaggca    6120
ccctcgataa tgataaattg gacattagat actagcatta cttattttgg tgttcttgtg    6180
ccagtggctt ccacgtattt cgtgtttgaa ttacatatgc tgctactttc tctgaccaat    6240
acgaataacg gtatgttacc agaagaaacc aaggtgacgg acagttttc catcgaaaac     6300 atcctatttc taataaagga gcggtcacta cccattggtc tttccaaatt actcgacttt    6360
tccataaaag tatcaacccct acaaagaacg gttgatacgg agcagtcatt ccaagtggaa    6420
agttctcatt tcagggtctg cttatctcct gattctctat taagattaat gtggggcgcg    6480
cataaattgc tagacttgag ccattactat tcaagacgcc atgcccctaa tatttggaac    6540
actaagatgt tcaccggtaa aagtgataag tcaaaagaaa tgcccataaa tttccgttca    6600
atacacatcc tgtcctataa attttgtatt gggtggatat tccagtatgg agcaggctcc    6660
aatcctgggt taatgttagg ttataacaga ttgttttcag catatgaaaa ggattttggg    6720
aaattcacag ttgtggacgc ttttttctct gttccgaatg gtaatacctc aagcactttt    6780
ttctctgaag gaaacgagaa agacaaatat aatagaagtt tcttgccaaa catgcaaata    6840
tcctactggt tcaaaagatg tggtgagttg aaagattggt tttttagatt tcatggtgaa    6900
gcactggatg taaactttgt cccgtcattc atggatgtca ttgagtctac tttacaatcc    6960
atgcgagcat tcaagagct gaaaaagaac attctggatg tgtccgagag tttgcgtgcg     7020
gaaaatgata attcttatgc tagtaccagt gtcgaaagtg cttcgagtag tttggctccc    7080
tttctcgata acattagatc tgttaactca aatttcaagt atgacggtgg tgtatttagg    7140
gtttacacgt acgaagatat tgaaaccaag agtgagccat cttttgaaat aaaaagtcca    7200
gtagtcacta taaactgtac atataaacat gatgaagata aagttaagcc acataaattc    7260
agaacattaa tcactgtcga cccaacgcat aatactttgt atgcaggatg tgctccttta    7320
ttaatggaat tttctgaaag tctgcaaaag atgataaaga aacatagcac cgacgaaaaa    7380
ccaaacttta caaaaccttc ttcgcagaat gttgattata agcgactttt ggatcaattt    7440
gatgtggctg taaaactaac atcagccaag caacagttaa gtttgagctg tgaaccaaaa    7500
gctaaggttc aggcagatgt tggatttgaa tcgttttgt tcagtatggc taccaatgag     7560
ttcgactctg aacagccttt ggagttttct ttaactctag aacacacaaa agcgtccatt    7620
aagcacatat tttcaagaga agtaagtacg tcctttgaag ttggtttcat ggacttgacg    7680
cttttattta cacatcctga tgtaatcagt atgtatggaa cggggttggt ttctgatcta    7740
agcgtcttct tcaatgtaaa gcagctccag aacctgtatt tattcttgga catatggagg    7800
ttcagtagca ttttacacac acggccagtg caaagaactg ttaataagga aattgaaatg    7860
```

-continued

```
agttgattaa catcaaccaa ctatgccgat gcaggtacgg aaatacccctg gtgctttaca      7920 ttaatttta caaatgttag cggagacgtt gatttgggtc cttctctcgg tatgatttca       7980
ttaaggacac aaagaacatg gctggccaca gatcattata acgagaagcg gcagttactg      8040
catgctttca ctgacggtat tagcttgaca tcagaaggta gactgagtgg tttatttgaa      8100
gttgcgaatg caagttggtt atcagaagta aaatggccac ctgaaaaaag caaaaatact      8160
catccattag tttccacctc cctgaatatt gatgatatag cggtaaaggc tgcttttgat      8220
tatcatatgt tcttaatcgg cactataagt aacatacact tccatcttca taatgaaaag      8280
gatgccaagg gggttctacc tgatttgctg caggtctctt tttcatcaga tgaaattatc      8340
ctcagctcta ctgcattagt tgtagcaaat atactggata tctacaacac cattgtacgt      8400
atgaggcagg ataataaaat atcgtatatg gagacgttga gagattccaa tcctggtgaa      8460
tctaggcaac caatattata caaagacatt ttaagatcgc tgaaactact cagaactgat      8520
ctctcggtga atatctcctc ttcaaaggtc cagatttcgc caatatcttt attcgatgtg      8580
gaagtgttag taataagaat tgaaaagtc tctatacgtt ccgaaacaca ttcggggaaa       8640
aaattaaaga cagatttgca actacaagtt ttagatgttt ctgcagcgct ttctacttcc      8700
aaagaagaat tagatgagga agttggagct tccattgcta ttgatgatta catgcattat      8760
gcttccaaga ttgtcggtgg tactatcatt gatattccaa aacttgctgt tcatatgaca      8820
actttacaag aagaaaagac aaataattta gaatatctat ttgcttgctc tttttcagac      8880
aaaatatctg taaggtggaa tctagggcct gtagacttca taaaggaaat gtggactaca      8940
catgtcaaag cactggcagt tcgtcgatcc caggtagcaa atatttcctt tggacaaact      9000
gaggaagaac ttgaagaatc aattaaaaag gaagaagccg cttcaaagtt taattatatt      9060
gcactagaag aaccgcagat cgaagtgcct cagataagag atctgggaga cgccactcca      9120
cctatggaat ggttttggtgt caatagaaaa aaatttccga aattcactca ccaaaccgca      9180
gttatccccg tccaaaagct tgtttatctt gcagaaaagc agtatgtcaa gatactagat      9240
gatacgcatt aatctcgttc ctaattatat tcaaaagtcc ttgataccat atttctggtt      9300
tatgttttat agttttnaa ctacgtgata tttgcatata gtatagattt cctacgcccc       9360
atatttatga atcttgcatt cgaattttgc ttcaaaaaac tttgtttaaa ttgtatttg       9420 agagtttgtt aagatataca tatactttct gttttggtg cattatcatt gacctttttt       9480 ttttattcc taactgctgc ccaaaagaag aaataaacag gcgggaattt gggtagtatc       9540
tttaaacttc tttgatagca tgatattaca atcagcaagt gctcttgaat tgattattgt      9600
actagctaat tctgtttaag a                                                9621
```

<210> SEQ ID NO 2
<211> LENGTH: 2496
<212> TYPE: PRT
<213> ORGANISM: Saccharomyes cerevisiae
<400> SEQUENCE: 2

```
Met Glu Ala Ile Ser Gln Leu Arg Gly Val Pro Leu Thr His Gln Lys
  1               5                  10                  15

Asp Phe Ser Trp Val Phe Leu Val Asp Trp Ile Leu Thr Val Val
             20                  25                  30

Cys Leu Thr Met Ile Phe Tyr Met Gly Arg Ile Tyr Ala Tyr Leu Val
         35                  40                  45

Ser Phe Ile Leu Glu Trp Leu Leu Trp Lys Arg Ala Lys Ile Lys Ile
     50                  55                  60
```

```
Asn Val Glu Thr Leu Arg Val Ser Leu Leu Gly Gly Arg Ile His Phe
 65                  70                  75                  80

Lys Asn Leu Ser Val Ile His Lys Asp Tyr Thr Ile Ser Val Leu Glu
                 85                  90                  95

Gly Ser Leu Thr Trp Lys Tyr Trp Leu Leu Asn Cys Arg Lys Ala Glu
                100                 105                 110

Leu Ile Glu Asn Asp Lys Ser Ser Ser Gly Lys Lys Ala Lys Leu Pro
            115                 120                 125

Cys Lys Ile Ser Val Glu Cys Glu Gly Leu Glu Ile Phe Ile Tyr Asn
130                 135                 140

Arg Thr Val Ala Tyr Asp Asn Val Ile Asn Leu Leu Ser Lys Asp Glu
145                 150                 155                 160

Arg Asp Lys Phe Glu Lys Tyr Leu Asn Glu His Ser Phe Pro Glu Pro
                165                 170                 175

Phe Ser Asp Gly Ser Ser Ala Asp Lys Leu Asp Glu Asp Leu Ser Glu
                180                 185                 190

Ser Ala Tyr Thr Thr Asn Ser Asp Ala Ser Ile Val Asn Asp Arg Asp
            195                 200                 205

Tyr Gln Glu Thr Asp Ile Gly Lys His Pro Lys Leu Leu Met Phe Leu
210                 215                 220

Pro Ile Glu Leu Lys Phe Ser Arg Gly Ser Leu Leu Gly Asn Lys
225                 230                 235                 240

Phe Thr Pro Ser Val Met Ile Leu Ser Tyr Glu Ser Gly Lys Gly Ile
                245                 250                 255

Ile Asp Val Leu Pro Pro Lys Glu Arg Leu Asp Leu Tyr Arg Asn Lys
            260                 265                 270

Thr Gln Met Glu Phe Lys Asn Phe Glu Ile Ser Ile Lys Gln Asn Ile
            275                 280                 285

Gly Tyr Asp Asp Ala Ile Gly Leu Lys Phe Lys Ile Asp Arg Gly Lys
            290                 295                 300

Val Ser Lys Leu Trp Lys Thr Phe Val Arg Val Phe Gln Ile Val Thr
305                 310                 315                 320

Lys Pro Val Val Pro Lys Lys Thr Lys Lys Ser Ala Gly Thr Ser Asp
                325                 330                 335

Asp Asn Phe Tyr His Lys Trp Lys Gly Leu Ser Leu Tyr Lys Ala Ser
                340                 345                 350

Ala Gly Asp Ala Lys Ala Ser Asp Leu Asp Asp Val Glu Phe Asp Leu
            355                 360                 365

Thr Asn His Glu Tyr Ala Lys Phe Thr Ser Ile Leu Lys Cys Pro Lys
            370                 375                 380

Val Thr Ile Ala Tyr Asp Val Asp Val Pro Gly Val Pro His Gly
385                 390                 395                 400

Ala His Pro Thr Ile Pro Asp Ile Asp Gly Pro Asp Val Gly Asn Asn
                405                 410                 415

Gly Ala Pro Pro Asp Phe Ala Leu Asp Val Gln Ile His Gly Gly Ser
                420                 425                 430

Ile Cys Tyr Gly Pro Trp Ala Gln Arg Gln Val Ser His Leu Gln Arg
            435                 440                 445

Val Leu Ser Pro Val Val Ser Arg Thr Ala Lys Pro Ile Lys Lys Leu
            450                 455                 460

Pro Pro Gly Ser Arg Arg Ile Tyr Thr Leu Phe Arg Met Asn Ile Ser
465                 470                 475                 480
```

-continued

```
Ile Met Glu Asp Thr Thr Trp Arg Ile Pro Thr Arg Glu Ser Ser Lys
            485                 490                 495

Asp Pro Glu Phe Leu Lys His Tyr Lys Glu Thr Asn Glu Glu Tyr Arg
            500                 505                 510

Pro Phe Gly Trp Met Asp Leu Arg Phe Cys Lys Asp Thr Tyr Ala Asn
            515                 520                 525

Phe Asn Ile Ser Val Cys Pro Thr Val Gln Gly Phe Gln Asn Asn Phe
530                 535                 540

His Val His Phe Leu Glu Thr Glu Ile Arg Ser Ser Val Asn His Asp
545                 550                 555                 560

Ile Leu Leu Lys Ser Lys Val Phe Asp Ile Asp Gly Asp Ile Gly Tyr
            565                 570                 575

Pro Leu Gly Trp Asn Ser Lys Ala Ile Trp Ile Asn Met Lys Ser
            580                 585                 590

Glu Gln Leu Glu Ala Phe Leu Leu Arg Glu His Ile Thr Leu Val Ala
            595                 600                 605

Asp Thr Leu Ser Asp Phe Ser Ala Gly Asp Pro Thr Pro Tyr Glu Leu
            610                 615                 620

Phe Arg Pro Phe Val Tyr Lys Val Asn Trp Glu Met Glu Gly Tyr Ser
625                 630                 635                 640

Ile Tyr Leu Asn Val Asn Asp His Asn Ile Val Asn Asn Pro Leu Asp
            645                 650                 655

Phe Asn Glu Asn Cys Tyr Leu Ser Leu His Gly Asp Lys Leu Ser Ile
            660                 665                 670

Asp Val Thr Val Pro Arg Glu Ser Ile Leu Gly Thr Tyr Thr Asp Met
            675                 680                 685

Ser Tyr Glu Ile Ser Thr Pro Met Phe Arg Met Met Leu Asn Thr Pro
            690                 695                 700

Pro Trp Asn Thr Leu Asn Glu Phe Met Lys His Lys Glu Val Gly Arg
705                 710                 715                 720

Ala Tyr Asp Phe Thr Ile Lys Gly Ser Tyr Leu Leu Tyr Ser Glu Leu
            725                 730                 735

Asp Ile Asp Asn Val Asp Thr Leu Val Ile Glu Cys Asn Ser Lys Ser
            740                 745                 750

Thr Val Leu His Cys Tyr Gly Phe Val Met Arg Tyr Leu Thr Asn Val
            755                 760                 765

Lys Met Asn Tyr Phe Gly Glu Phe Phe Asn Phe Val Thr Ser Glu Glu
770                 775                 780

Tyr Thr Gly Val Leu Gly Ala Arg Glu Val Gly Asp Val Thr Lys
785                 790                 795                 800

Ser Ser Val Ala Asp Leu Ala Ser Thr Val Asp Ser Gly Tyr Gln Asn
            805                 810                 815

Ser Ser Leu Lys Asn Glu Ser Glu Asp Lys Gly Pro Met Lys Arg Ser
            820                 825                 830

Asp Leu Lys Arg Thr Thr Asn Glu Thr Asp Ile Trp Phe Thr Phe Ser
            835                 840                 845

Val Trp Asp Gly Ala Leu Ile Leu Pro Glu Thr Ile Tyr Ser Phe Asp
850                 855                 860

Pro Cys Ile Ala Leu His Phe Ala Glu Leu Val Val Asp Phe Arg Ser
865                 870                 875                 880

Cys Asn Tyr Tyr Met Asp Ile Met Ala Val Leu Asn Gly Thr Ser Ile
                        885                 890                 895

Lys Arg His Val Ser Lys Gln Ile Asn Glu Val Phe Asp Phe Ile Arg
```

-continued

```
                900             905             910
Arg Asn Asn Gly Ala Asp Glu Gln Glu His Gly Leu Leu Ser Asp Leu
            915             920             925

Thr Ile His Gly His Arg Met Tyr Gly Leu Pro Pro Thr Glu Pro Thr
    930             935             940

Tyr Phe Cys Gln Trp Asp Ile Asn Leu Gly Asp Leu Cys Ile Asp Ser
945             950             955             960

Asp Ile Glu Phe Ile Lys Gly Phe Phe Asn Ser Phe Lys Ile Gly
                965             970             975

Phe Gly Tyr Asn Asp Leu Glu Asn Ile Leu Leu Tyr Asp Thr Glu Thr
            980             985             990

Ile Asn Asp Met Thr Ser Leu Thr Val His Val Glu Lys Ile Arg Ile
    995             1000            1005

Gly Leu Lys Asp Pro Val Met Lys Ser Gln Ser Val Ile Ser Ala Glu
        1010            1015            1020

Ser Ile Leu Phe Thr Leu Ile Asp Phe Glu Asn Glu Lys Tyr Ser Gln
1025            1030            1035            1040

Arg Ile Asp Val Lys Ile Pro Lys Leu Thr Ile Ser Leu Asn Cys Val
            1045            1050            1055

Met Gly Asp Gly Val Asp Thr Ser Phe Leu Lys Phe Glu Thr Lys Leu
            1060            1065            1070

Arg Phe Thr Asn Phe Glu Gln Tyr Lys Asp Ile Asp Lys Lys Arg Ser
            1075            1080            1085

Glu Gln Arg Arg Tyr Ile Thr Ile His Asp Ser Pro Tyr His Arg Cys
            1090            1095            1100

Pro Phe Leu Leu Pro Leu Phe Tyr Gln Asp Ser Asp Thr Tyr Gln Asn
1105            1110            1115            1120

Leu Tyr Gly Ala Ile Ala Pro Ser Ser Ser Ile Pro Thr Leu Pro Leu
            1125            1130            1135

Pro Thr Leu Pro Asp Thr Ile Asp Tyr Ile Ile Glu Asp Ile Val Gly
            1140            1145            1150

Glu Tyr Ala Thr Leu Leu Glu Thr Thr Asn Pro Phe Lys Asn Ile Phe
            1155            1160            1165

Ala Glu Thr Pro Ser Thr Met Glu Pro Ser Arg Ala Ser Phe Ser Glu
            1170            1175            1180

Asp Asp Asn Glu Glu Gly Ala Asp Pro Ser Ser Phe Lys Pro Val Ala
1185            1190            1195            1200

Phe Thr Glu Asp Arg Asn His Glu Arg Asp Asn Tyr Val Val Asp Val
            1205            1210            1215

Ser Tyr Ile Leu Leu Asp Val Asp Pro Leu Leu Phe Ile Phe Ala Lys
            1220            1225            1230

Ser Leu Leu Glu Gln Leu Tyr Ser Glu Asn Met Val Gln Val Leu Asp
            1235            1240            1245

Asp Ile Glu Ile Gly Ile Val Lys Arg Leu Ser Asn Leu Gln Glu Gly
            1250            1255            1260

Ile Thr Ser Ile Ser Asn Ile Asp Ile His Ile Ala Tyr Leu Asn Leu
1265            1270            1275            1280

Ile Trp Gln Glu Thr Gly Glu Glu Gly Phe Glu Leu Tyr Leu Asp Arg
            1285            1290            1295

Ile Asp Tyr Gln Met Ser Glu Lys Ser Leu Glu Lys Asn Arg Thr Asn
            1300            1305            1310

Lys Leu Leu Glu Val Ala Ala Leu Ala Lys Val Lys Thr Val Arg Val
            1315            1320            1325
```

```
Thr Val Asn Gln Lys Lys Asn Pro Asp Leu Ser Glu Asp Arg Pro Pro
    1330                1335                1340
Ala Leu Ser Leu Gly Ile Glu Gly Phe Glu Val Trp Ser Ser Thr Glu
1345                1350                1355                1360
Asp Arg Gln Val Asn Ser Leu Asn Leu Thr Ser Ser Asp Ile Thr Ile
                1365                1370                1375
Asp Glu Ser Gln Met Glu Trp Leu Phe Glu Tyr Cys Ser Asp Gln Gly
            1380                1385                1390
Asn Leu Ile Gln Glu Val Cys Thr Ser Phe Asn Ser Ile Gln Asn Thr
        1395                1400                1405
Arg Ser Asn Ser Lys Thr Glu Leu Ile Ser Lys Leu Thr Ala Ala Ser
    1410                1415                1420
Glu Tyr Tyr Gln Ile Ser His Asp Pro Tyr Val Ile Thr Lys Pro Ala
1425                1430                1435                1440
Phe Ile Met Arg Leu Ser Lys Gly His Val Arg Glu Asn Arg Ser Trp
                1445                1450                1455
Lys Ile Ile Thr Arg Leu Arg His Ile Leu Thr Tyr Leu Pro Asp Asp
            1460                1465                1470
Trp Gln Ser Asn Ile Asp Glu Val Leu Lys Glu Lys Tyr Thr Ser
        1475                1480                1485
Ala Lys Asp Ala Lys Asn Ile Phe Met Ser Val Phe Ser Thr Trp Arg
    1490                1495                1500
Asn Trp Glu Phe Ser Asp Val Ala Arg Ser Tyr Ile Tyr Gly Lys Leu
1505                1510                1515                1520
Phe Thr Ala Glu Asn Glu Lys His Lys Gln Asn Leu Ile Lys Lys Leu
                1525                1530                1535
Leu Lys Cys Thr Met Gly Ser Phe Tyr Leu Thr Val Tyr Gly Glu Gly
            1540                1545                1550
Tyr Glu Val Glu His Asn Phe Val Ala Asp Ala Asn Leu Val Val
        1555                1560                1565
Asp Leu Thr Pro Pro Val Thr Ser Leu Pro Ser Asn Arg Glu Glu Thr
    1570                1575                1580
Ile Glu Ile Thr Gly Arg Val Gly Ser Val Lys Gly Lys Phe Ser Asp
1585                1590                1595                1600
Arg Leu Leu Lys Leu Gln Asp Leu Ile Pro Leu Ile Ala Ala Val Gly
                1605                1610                1615
Glu Asp Asp Lys Ser Asp Pro Lys Glu Leu Ser Lys Gln Phe Lys
            1620                1625                1630
Met Asn Thr Val Leu Leu Val Asp Lys Ser Glu Leu Gln Leu Val Met
        1635                1640                1645
Asp Gln Thr Lys Leu Ile Ser Arg Thr Val Gly Gly Arg Val Ser Leu
    1650                1655                1660
Leu Trp Glu Asn Leu Lys Asp Ser Thr Ser Gln Ala Gly Ser Leu Val
1665                1670                1675                1680
Ile Phe Ser Gln Lys Ser Glu Val Trp Leu Lys His Thr Ser Val Ile
                1685                1690                1695
Leu Gly Glu Ala Gln Leu Arg Asp Phe Ser Ile Leu Ala Thr Thr Glu
            1700                1705                1710
Ala Trp Ser His Lys Pro Thr Ile Leu Ile Asn Asn Gln Cys Ala Asp
        1715                1720                1725
Leu His Phe Arg Ala Met Ser Ser Thr Glu Gln Leu Val Thr Ala Ile
    1730                1735                1740
```

-continued

```
Thr Glu Ile Arg Glu Ser Leu Met Met Ile Lys Glu Arg Ile Lys Phe
1745                1750                1755                1760

Lys Pro Lys Ser Lys Lys Ser Gln Phe Val Asp Gln Lys Ile Asn
            1765                1770                1775

Thr Val Leu Ser Cys Tyr Phe Ser Asn Val Ser Ser Glu Val Met Pro
            1780                1785                1790

Leu Ser Pro Phe Tyr Ile Arg His Glu Ala Lys Gln Leu Asp Ile Tyr
            1795                1800                1805

Phe Asn Lys Phe Gly Ser Asn Glu Ile Leu Leu Ser Ile Trp Asp Thr
            1810                1815                1820

Asp Phe Phe Met Thr Ser His Gln Thr Lys Glu Gln Tyr Leu Arg Phe
1825                1830                1835                1840

Ser Phe Gly Asp Ile Glu Ile Lys Gly Gly Ile Ser Arg Glu Gly Tyr
            1845                1850                1855

Ser Leu Ile Asn Val Asp Ile Ser Ile Ser Met Ile Lys Leu Thr Phe
            1860                1865                1870

Ser Glu Pro Arg Arg Ile Val Asn Ser Phe Leu Gln Asp Glu Lys Leu
            1875                1880                1885

Ala Ser Gln Gly Ile Asn Leu Leu Tyr Ser Leu Lys Pro Leu Phe Phe
            1890                1895                1900

Ser Ser Asn Leu Pro Lys Lys Glu Lys Gln Ala Pro Ser Ile Met Ile
1905                1910                1915                1920

Asn Trp Thr Leu Asp Thr Ser Ile Thr Tyr Phe Gly Val Leu Val Pro
            1925                1930                1935

Val Ala Ser Thr Tyr Phe Val Phe Glu Leu His Met Leu Leu Leu Ser
            1940                1945                1950

Leu Thr Asn Thr Asn Asn Gly Met Leu Pro Glu Glu Thr Lys Val Thr
            1955                1960                1965

Gly Gln Phe Ser Ile Glu Asn Ile Leu Phe Leu Ile Lys Glu Arg Ser
            1970                1975                1980

Leu Pro Ile Gly Leu Ser Lys Leu Leu Asp Phe Ser Ile Lys Val Ser
1985                1990                1995                2000

Thr Leu Gln Arg Thr Val Asp Thr Glu Gln Ser Phe Gln Val Glu Ser
            2005                2010                2015

Ser His Phe Arg Val Cys Leu Ser Pro Asp Ser Leu Leu Arg Leu Met
            2020                2025                2030

Trp Gly Ala His Lys Leu Leu Asp Leu Ser His Tyr Tyr Ser Arg Arg
            2035                2040                2045

His Ala Pro Asn Ile Trp Asn Thr Lys Met Phe Thr Gly Lys Ser Asp
            2050                2055                2060

Lys Ser Lys Glu Met Pro Ile Asn Phe Arg Ser Ile His Ile Leu Ser
2065                2070                2075                2080

Tyr Lys Phe Cys Ile Gly Trp Ile Phe Gln Tyr Gly Ala Gly Ser Asn
            2085                2090                2095

Pro Gly Leu Met Leu Gly Tyr Asn Arg Leu Phe Ser Ala Tyr Glu Lys
            2100                2105                2110

Asp Phe Gly Lys Phe Thr Val Val Asp Ala Phe Phe Ser Val Pro Asn
            2115                2120                2125

Gly Asn Thr Ser Ser Thr Phe Phe Ser Glu Gly Asn Glu Lys Asp Lys
            2130                2135                2140

Tyr Asn Arg Ser Phe Leu Pro Asn Met Gln Ile Ser Tyr Trp Phe Lys
2145                2150                2155                2160

Arg Cys Gly Glu Leu Lys Asp Trp Phe Phe Arg Phe His Gly Glu Ala
```

-continued

```
                        2165                    2170                    2175
Leu Asp Val Asn Phe Val Pro Ser Phe Met Asp Val Ile Glu Ser Thr
                2180                    2185                    2190
Leu Gln Ser Met Arg Ala Phe Gln Glu Leu Lys Lys Asn Ile Leu Asp
        2195                    2200                    2205
Val Ser Glu Ser Leu Arg Ala Glu Asn Asp Asn Ser Tyr Ala Ser Thr
    2210                    2215                    2220
Ser Val Glu Ser Ala Ser Ser Ser Leu Ala Pro Phe Leu Asp Asn Ile
2225                    2230                    2235                    2240
Arg Ser Val Asn Ser Asn Phe Lys Tyr Asp Gly Gly Val Phe Arg Val
                2245                    2250                    2255
Tyr Thr Tyr Glu Asp Ile Glu Thr Lys Ser Glu Pro Ser Phe Glu Ile
            2260                    2265                    2270
Lys Ser Pro Val Val Thr Ile Asn Cys Thr Tyr Lys His Asp Glu Asp
        2275                    2280                    2285
Lys Val Lys Pro His Lys Phe Arg Thr Leu Ile Thr Val Asp Pro Thr
    2290                    2295                    2300
His Asn Thr Leu Tyr Ala Gly Cys Ala Pro Leu Leu Met Glu Phe Ser
2305                    2310                    2315                    2320
Glu Ser Leu Gln Lys Met Ile Lys Lys His Ser Thr Asp Glu Lys Pro
                2325                    2330                    2335
Asn Phe Thr Lys Pro Ser Ser Gln Asn Val Asp Tyr Lys Arg Leu Leu
            2340                    2345                    2350
Asp Gln Phe Asp Val Ala Val Lys Leu Thr Ser Ala Lys Gln Gln Leu
        2355                    2360                    2365
Ser Leu Ser Cys Glu Pro Lys Ala Lys Val Gln Ala Asp Val Gly Phe
    2370                    2375                    2380
Glu Ser Phe Leu Phe Ser Met Ala Thr Asn Glu Phe Asp Ser Glu Gln
2385                    2390                    2395                    2400
Pro Leu Glu Phe Ser Leu Thr Leu Glu His Thr Lys Ala Ser Ile Lys
                2405                    2410                    2415
His Ile Phe Ser Arg Glu Val Ser Thr Ser Phe Glu Val Gly Phe Met
            2420                    2425                    2430
Asp Leu Thr Leu Leu Phe Thr His Pro Asp Val Ile Ser Met Tyr Gly
        2435                    2440                    2445
Thr Gly Leu Val Ser Asp Leu Ser Val Phe Phe Asn Val Lys Gln Leu
    2450                    2455                    2460
Gln Asn Leu Tyr Leu Phe Leu Asp Ile Trp Arg Phe Ser Ser Ile Leu
2465                    2470                    2475                    2480
His Thr Arg Pro Val Gln Arg Thr Val Asn Lys Glu Ile Glu Met Ser
                2485                    2490                    2495
```

COLD-SENSITIVE BREAD-MAKING YEASTS

This application is a 371 of PCT/FR97/00254, filed Feb. 7, 1997.

The present invention relates to novel strains of cold-sensitive yeasts and methods of using these strains in bread-making.

Cold-sensitive mutants of *Saccharomyces cerevisiae*, i.e. mutants that are sensitive to low positive temperatures between 0 and 15° C., have been described abundantly in the scientific literature since long ago. There are various corresponding mutation sites, and many different phenotypes can be obtained. The mutation can affect growth in the cold, or fermentation in the cold, or both, this lack of growth and/or of fermentation can vary depending on the sugars present, it can be reversible or irreversible, i.e. it may or may not disappear when the temperature rises. The use of mutants in bread-making, for which fermentation of the sugars in the dough is limited in the cold but is restored at at least 20° C., has mainly been studied with the aim of obtaining dough for croissants or for Viennese bread and buns, or dough for pizza bases intended to be used by the housewife as a fresh product, i.e. after storage at refrigeration temperatures, in principle at +4° C., but in practice between 0 and +12° C. or more, in the distribution network, then until it is used. Preferably these refrigerated doughs for the housewife are ready to bake. In this connection we can cite the two European Patent Applications EP 487878 and EP 663441 and the International Patent Applications WO 93/01724 and WO 94/19955.

In the first two documents cited, documents EP 487878 and EP 663441, where much attention is paid to blocking the fermentation of maltose, nearly all of the measurements of $CO_2$ release at different temperatures as a function of time are effected on a maltose-containing synthetic medium, where maltose is the only fermentable sugar. The main application described is a pizza dough that can be stored at refrigerator temperatures, and which by reason of this storage is ready to bake by the housewife.

In International Patent Applications WO 93/01724 and WO 94/19955, several means are described for obtaining doughs intended for the housewife, and which can be stored for a long time at low temperature. The use of so-called lts mutants (lts: low-temperature sensitive), which are available from university collection centres such as the Yeast Genetic Stock Center of the Donner Laboratory in the Department of Cellular and Molecular Biology of the University of California at Berkeley, is one of the options that has been investigated, the preferred solution apparently being to use strains that are unable to ferment glucose, but which can ferment either fructose or galactose, the sugar that is intended to be fermented being present in just the right amount to ensure the desired rise of the dough.

European Patent Application EP 667099 describes the production, and use in bread-making, of a cold-sensitive mutant obtained from a commercial strain of traditional baker's yeast for sugar-containing doughs, i.e. a slow strain that is not adapted to maltose. For the record, we can also cite patent application EP 556905 which is restricted to the description of various procedures that are likely in theory to enable cold-sensitive mutants to be obtained.

This copious literature has given rise to very few practical applications. Only two examples can be cited:

the marketing in Europe of a pizza dough that can be kept in cold storage for a long time and is ready to bake after this cold storage;

the rather limited marketing in Japan, at a very high price, of a yeast for sugar-containing doughs, whose fermentation activity is slowed down at low temperature.

It should be mentioned that production of pizza dough generally requires yeasts of low activity with respect to release of gas, the primary role of the yeast being the supply of aromas. It should be noted that the strain marketed in Japan is a slow-working strain that is not adapted to maltose, whereas the strains generally used throughout the world for the production of bread-making yeasts are maltose-adapted fast-working strains.

The invention relates to novel strains obtained by classical mutation techniques and which exhibit progress relative to the state of the art, fresh and dry bread-making yeasts obtained with these strains, and the application of these strains in various methods of bread-making or production of other bakery products, especially breads of the French type.

The invention also relates to novel strains obtained by directed mutagenesis, effected by molecular biology, consisting of reproducing, specifically in industrial strains of bread-making yeasts, or in the starting haploids that served for construction of the said industrial strains, the mutations, monogenic or not, giving the required phenotype in the strains selected after conventional mutation treatment, for example with chemical agents. One variant, according to the invention, of construction of strains whose fermentation is blocked at low temperature and is restored above 20° C. is the transformation of industrial strains of bread-making yeast with a gene selected because it has a direct or indirect action on the fermentation of sugars, and whose expression is temperature-dependent.

The invention relates in particular to a novel strain of bread-making yeast giving fresh or dry yeasts that can be described as fast-working yeasts at 30° C. on dough without addition of sugar, i.e. fresh yeasts giving at least 100 ml of $CO_2$ in the $A_1$ test in 2 hours at 30° C., preferably at least 110 ml of $CO_2$ and more preferably at least 150 ml. Moreover, these novel fresh and dry yeasts conform to the following ratio:

$$\frac{\text{release of } CO_2 \text{ in 48 hours at } 8° \text{ C. in the test } A_1}{\text{release } CO_2 \text{ in 2 hours at } 30° \text{ C. in the test } A_1} =$$

less than 45% and preferably less than 40% and even more preferably less than 30%. Preferably, these novel fresh and dry yeasts conform to the same percentages, if this ratio is measured with the $A_5$ test, and preferably with this $A_5$ test this ratio will be less than or equal to 20%.

The invention also relates to the use of novel strains obtained in deferred bakery methods for production of bread, especially bread of the French type or bread with low sugar content, i.e. with less than 5% of sugar.

A deferred bakery method is defined as any method where there is a period of more than 6 hours between kneading and baking, and generally more than 12 hours. In particular, the use of fresh or dry yeasts obtained with a cold-sensitive strain of baker's yeast represents an important advance in all processes of deferred bread-making such as the slow-rising or blocked-rising methods defined below; this use leads reliably to lumps of dough that remain ready to bake for a period of at least 4 hours, and preferably at least 8 hours, giving faultless baked products.

Finally the invention relates to novel bakery techniques, such as methods of production of leaven or the use of bulk doughs, based on the use of cold-sensitive baker's yeasts.

The following are the brief descriptions of the drawings.

Figure 1:
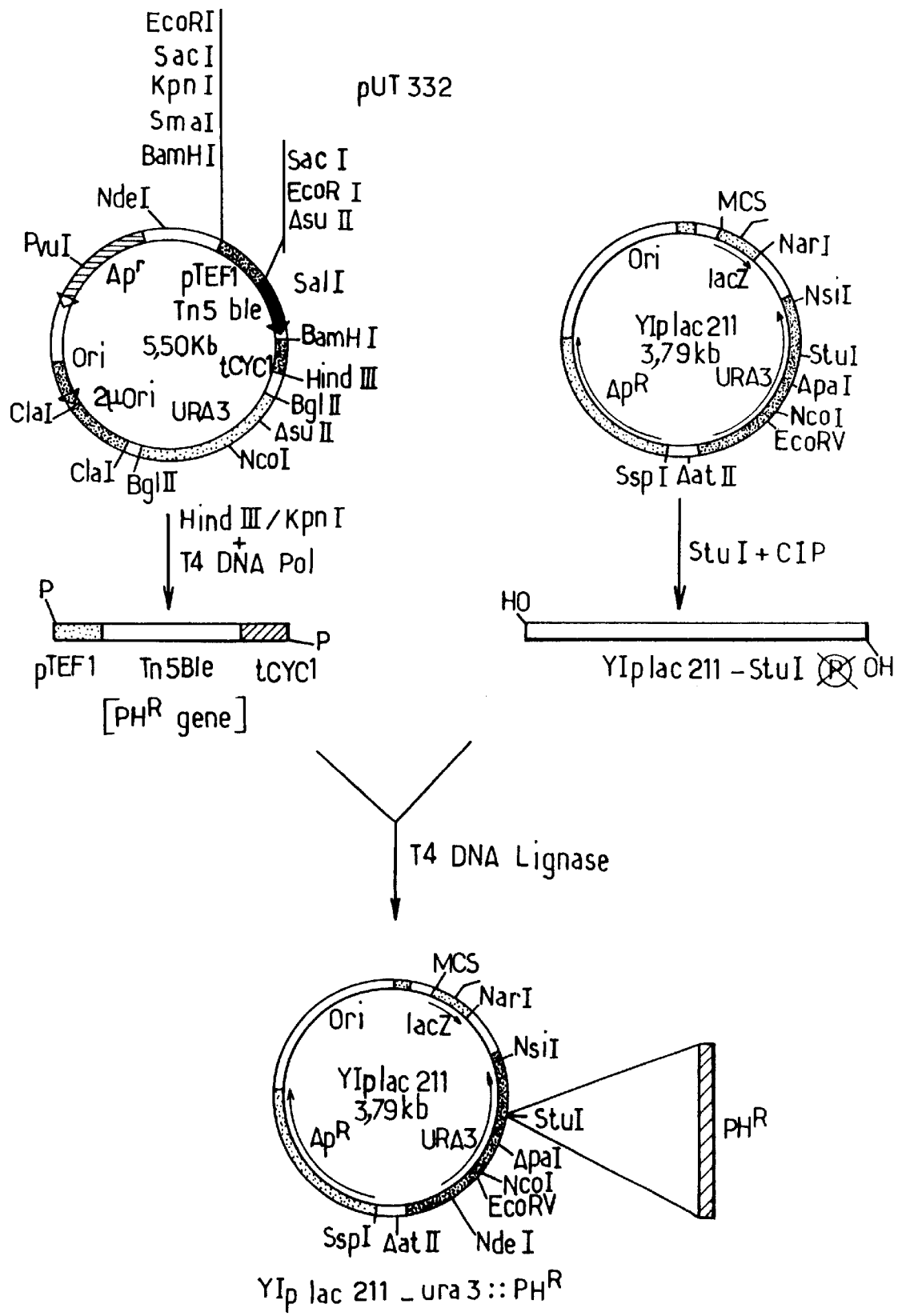
FIG. 1 is a diagrammatic representation of the construction of the plasmid Yip lac 211-ura::$PH^R$.

The drawings are provided in order to assist in the understanding of the present invention when viewed in conjunction with the detailed description.

The tests used by the Applicant for characterization of the aforementioned yeasts are carried out with the aid of the Burrows and Harrison fermentometer described in the "Journal of the Institute of Brewing", Vol. LXV, No. 1, January–February 1959 and are defined precisely as follows:

Test $A_1$ (fresh compressed yeasts).

To 20 g of flour incubated at the temperature chosen for the measurements, add a weight of compressed yeast corresponding to 160 mg of dry matter, this yeast being mixed in 15 ml of water containing 27 g of NaCl per liter and 4 g of $(NH_4)_2SO_4$ per liter; mix with a spatula for 40 seconds, so as to obtain a dough, which is placed on a bain-marie set at the chosen temperature; thirteen minutes after the start of mixing, the vessel containing the dough is sealed hermetically; the total amount of gas produced is measured after 60, then 120 minutes or several hours; this quantity is expressed in ml at 20° C. and 760 mmHg.

For all yeasts capable of giving a release of gas equal to or greater than 150 ml of $CO_2$ in 120 minutes, the quantity of fermentable sugars supplied solely by the flour is limiting; accordingly, the test is modified as follows: add a weight of yeast corresponding to 106 mg of yeast dry matter, instead of 160 mg, and the reading of the amount of gas produced is conventionally multiplied by 1.5.

Test $A'_1$ (dry yeasts).

Identical to test $A_1$, except that prior to kneading, the 160 mg of yeast dry matter that is in the form of active dry yeast is rehydrated for 15 minutes in distilled water at 38° C., using for this purpose 40% of the volume of hydration water employed; the extra water, with an addition of 405 mg of NaCl, is added at the end of the 15 minutes of rehydration.

Test $A_3$ (fresh compressed yeasts).

Test identical to test $A_1$, except that 2 g of sucrose is added to the flour; the total amount of gas produced is measured after 60 minutes, 120 minutes or several hours.

Test $A'_3$ (dry yeasts).

Test identical to test $A'_1$, except that 2 g of sucrose is added to the flour; the total amount of gas produced is measured after 60 minutes, 120 minutes or several hours.

Test $A_5$ (fresh compressed yeasts).

Test identical to test $A_1$, except that 4 g of sucrose is added to the flour; the total amount of gas produced is measured after 60 minutes and 120 minutes or several hours.

Test $A'_5$ (dry yeasts).

Test identical to test $A'_1$, except that 4 g of sucrose is added to the flour; the total amount of gas produced is measured after 60 minutes and 120 minutes or several hours.

Test $A_6$ (fresh compressed yeasts).

To 25 g of flour incubated at 30° C., add 6.5 g of icing sugar and a weight of compressed yeast corresponding to 320 mg of dry matter, then proceed as for test $A_1$ and the total amount of gas produced is measured after 60 and 120 minutes or several hours.

Test $A'_6$ (dry yeasts).

Test identical to test $A_6$, with the procedure for rehydrating the 320 mg of yeast dry matter in the form of active dry yeast as in test $A'_1$.

The following culture media are used:

YPG: 20 g/l glucose, 20 g/l bactopeptone, 10 g/l yeast extract.

YPM: 20 g/l maltose, 20 g/l bactopeptone, 10 g/l yeast extract.

YPM/G: 20 g/l maltose, 2 g/l glucose, 20 g/l bactopeptone, 10 g/l yeast extract.

YEG-Agar: 20 g/l glucose, 5 g/l yeast extract, 30 g/l agar.

The following procedure is used for constructing the new strains according to the invention.

In the first stage, select the parent strains that will be submitted to the mutation treatment. It is preferable to select strains that are already known to be used industrially for the production of baker's yeasts, as these strains already possess the essential basic properties; most of these strains can be obtained from international collections and especially the ATCC (American Type Culture Collection), where they are lodged. They can also be isolated from commercial fresh or dry baker's yeasts.

They can be divided into three main groups:

strains that are fast-working on sugar-free dough, i.e. well-adapted to maltose which have maltose permease and maltase activities, constitutive and not repressed by glucose;

slow-working strains well adapted to sugar-containing doughs, osmotolerant strains that have low or very low maltose permease and/or maltase activities after culture on glucose;

strains constructed to combine the properties of the preceding two groups, such as those described in European Patent Application No. 92 401168.7 of Apr. 23, 1992 published under No. 0 511 108.

The best strains of baker's yeasts known so far in these different groups are selected as the parent strains. A strain will generally be less active at low temperature, the lower its activity at 30° C., the temperature usually employed for measurements of fermentation activity. If, in the final application, there is no need for high fermentation activity, it is beneficial to start from low-performance strains that are not adapted to maltose, so as to find, after mutagenesis, mutants whose fermentation will be slower at low temperature relative to the parent strain. That is why the prior art generally instructs that we should not start from fast-working maltose-adapted strains. However, these strains can only be of interest for very specific applications. According to the present invention, the parent strains submitted to the mutagenesis treatment will preferably be fast-working strains that are well adapted to maltose. These strains, diploid or polyploid, will generally be polyploid strains.

These diploid or polyploid strains thus selected are then submitted to a conventional mutagenesis treatment, for example using chemical agents. The mutants obtained are incubated on a conventional glucose medium such as YPG medium, in aerobic conditions (agitated flasks), for several hours at 30° C., and are then submitted to initial selection by strictly anaerobic culture on a glucose-containing medium enriched with nystatin or any agent that is known to kill cells that possess metabolic activity, these strictly anaerobic cultures being effected at a temperature selected between 10° C. and 15° C. Then the cell suspension resulting from enrichment with nystatin or any similar agent is spread out at an appropriate dilution to obtain isolated colonies of the mutants that have not been killed because they do not have metabolic activity at the chosen temperature between 10 and 15° C. Agents equivalent to nystatin are for example the tritium derivatives described by LITTLEWOOD, B. S. and DAVIES, J. E. in the article "Enrichment for temperature sensitive and auxotrophic mutants in *Saccharomyces cerevisiae* by Tritium suicide", Mutation Research 1973, 17, 315–322.

The diploid or polyploid strains obtained according to the classical method of mutagenesis described above are selected by measuring their consumption of various sugars in anaerobiosis at low temperature.

The various sugars involved in bread-making fermentation are described below. In doughs consisting solely of flour, water, salt and yeast (bread-making of the French type), we generally find:

less than 0.1% by weight, relative to the flour, of directly fermentable simple hexoses, essentially in the form of glucose;

a little less than or about 1% of simple hexoses (glucose and fructose) released by the action of the invertase of the yeast;

a few percent of maltose (of the order of 2 to 3%) resulting from the action of the amylases present in the dough. Maltose is the principal sugar, and it must be fermented at the same time, or at least without delay after consumption of the fructose and glucose released by the invertase of the yeast. It should be noted that unless we start with a yeast strain without invertase, on commencement of bread-making fermentation there will always be glucose and fructose present at the same time as maltose. In doughs to which sugars have been added, this is either sucrose, glucose, or isoglucose (mixture of glucose and fructose). The sucrose is inverted to glucose and fructose by the invertase of the yeast.

According to the selection tests used for carrying out the present invention, a known biomass of diploid or polyploid mutants selected as described above is tested by measuring the consumption, by this biomass, of glucose (glucose-containing medium) or of maltose and glucose (maltose-containing medium with a little glucose) or of maltose alone in anaerobiosis at a temperature leading to sensitization to the cold, preferably between 8 and 15° C., for a time such that about 90% of the sugars present in the medium are consumed by the starting, parent strain. The residual sugars are determined using the sodium dinitrosalicylate reagent.

This selection test can be carried out advantageously in the following manner. The mutants selected as described above, after culture in conditions that kill the cells possessing an active metabolism in anaerobic conditions at a temperature selected between 10 and 15° C., are cultivated on YEG-AGAR medium for 24 hours. The biomasses obtained are harvested so as to obtain a suspension in distilled water with constant optical density, for example 15, which corresponds to about 7 mg of dry matter of yeast biomass per milliliter. 10 microliters of this yeast suspension are incubated in the presence of 100 microliters of culture medium on microtitration plates, one microtitration plate permitting the testing of at least 90 mutants at a time. The microtitration plates are then incubated at the chosen temperature, for a time such that the control or controls consume 90% of the control sugars. The sugars present are determined by adding 100 µl per well or cup of 1% sodium dinitrosalicylate reagent after heating the microtitration plate at 55° C. for 30 min. The consumption of starting sugars can be measured:

either by direct measurement of absorption at 550 nanometers by a microtitration plate reader after transfer of the yeast-free reaction medium to another microtitration plate, or by measurement with the spectrophotometer at 550 nm after dilution of the reaction medium to one tenth.

For this measurement, the mutants are selected which, on the YPM/G medium, consume less than 60% of the sugar consumed by the control.

These tests can also be effected on YPG medium or on YPM medium.

This selection procedure made it possible, among other things, to obtain the following three strains which have been lodged with the National Centre for Culture of Microorganisms (Centre National de Culture de Microorganismes, CNCM), Pasteur Institute, Paris:

strain S47-12b1 lodged with the CNCM under No. I-1645, on May 12, 1995, strain L30-13 lodged with the CNCM under No. I-1647, on May 12, 1995, strain L30-91 lodged with the CNCM under No. I-1646, on May 12, 1995.

Strain S47-12b1 is a mutant of a strain of fast-working, maltose-adapted yeast, which is used industrially for the production of bread-making yeasts.

With this strain S47-12b1 it is possible to obtain compressed fresh yeasts of the commercial fast-working type when it is used in normal conditions. It makes it possible to obtain compressed fresh yeasts which, when they are cultivated in such a way as to contain 7% nitrogen relative to dry matter, give at least 100 ml of $CO_2$ in test $A_1$ in 2 hours at 30° C. and preferably at least 110 ml, and which, when they are cultivated so as to contain 8.2% nitrogen relative to dry matter, give at least 150 ml of $CO_2$ in test $A_1$ in 2 hours at 30° C., and preferably at least 160 ml of $CO_2$. This strain makes it possible to obtain dry yeasts giving at least 100 ml of $CO_2$ in test $A_1$ in 2 hours at 30° C. Furthermore, these fresh yeasts have the property of complying with the ratios:

$$\frac{\text{release of } CO_2 \text{ in 48 hours at 8° C. in the test } A_1}{\text{release of } CO_2 \text{ in 2 hours at 30° C. in the test } A_1} \text{ of the order of } 40\%$$

$$\frac{\text{release of } CO_2 \text{ in 2 hours at 30° C. in the test } A_5}{\text{release of } CO_2 \text{ in 48 hours at 8° C. in the test } A_5} \text{ of the order of } 20\%$$

whereas these ratios are more than 100% for the fresh yeasts obtained with the parent strain, these fresh yeasts always being available commercially, very commonly and ordinarily, in Europe.

These ratios are also verified for the dry yeasts obtained with this strain.

Strains L30-13 and L30-91, lodged with the CNCM under No. I-1647 and I-1646 respectively, are mutants of an osmotolerant strain used industrially for the production of bread-making yeasts for sugar-containing doughs, marketed in the usual way on the European market. With these two strains it is possible to obtain compressed fresh yeasts or dry yeasts that are comparable to the commercial yeasts obtained with the parent strain. Moreover these yeasts have the property of complying with the following ratios:

Ratio between 48 hours of fermentation at 8° C./ 2 hours of fermentation at 30° C. expressed in %

|  | test $A_1$ | test $A_5$ |
|---|---|---|
| L30-13 | 20% | 3% |
| L30-91 | 5% | 1% | whereas these two ratios are more than 100% for the fresh bread-making yeasts obtained with the starting parent strain.

Strain S47-12b1 is a mutant of a fast-working strain which has retained, above 20° C., all of the properties of the "commercial" strain from which it was derived. It is particularly useful in deferred bread-making of the French type, i.e. in bread-making where little or no sugar is added to the dough.

This strain is particularly interesting for use in a traditional method of controlled rise in which fermentation is blocked after shaping the dough and before the last fermentation or finishing. This blocking of fermentation can be effected at higher temperature than usually, up to at least 8° C. or 10° C. or at the same temperature as usually (between −2° C. and +4° C.) but for longer times than usually. It is also particularly useful in so-called blocked-rise or slow-rise methods. Blocked rise is a method in which fermentation is blocked after finishing, just before placing in the oven. Strain S47-12b1 permits blocking of 4 to 24 hours at about 8° C. (i.e. between 4 and 10° C.). Slow rise is a method in which the finishing is very slow, and is effected at temperatures between 10 and 18° C., or about 15° C. for 15 to 24 hours. These two methods are useful as they provide a very wide range for placing in the oven, so that cooking can be spread over time, so that hot loaves that have just been baked can be offered all the time, without all the drawbacks of resorting to freezing.

Strains L30-13 and L30-91 are particularly useful for making bread from sugar-containing dough. With these two strains it is possible to carry out all forms of deferred bread-making from sugar-containing dough with the advantages connected with their phenotype of sensitivity to low temperature. Strain L30-91 is particularly useful for all doughs intended for the housewife, owing to its extremely low fermentation activity at 8° C. These two strains permit, in particular, the preparation of doughs for Viennese bread and buns, especially croissants for the housewife, as they can be kept for 1 month at 8° C., these doughs being baked after finishing over night at 20° C.

The bread-making yeasts obtained with these cold-sensitive strains are also useful for making frozen lumps of dough, as they make it easier to block any commencement of fermentation during kneading, division and shaping of the dough, effected at low temperature, as it is well known that the metabolites resulting from fermentation in bread-making are toxic to the yeast cells present in the frozen lumps of dough.

In general, cold-sensitive bread-making yeasts can be a considerable help in the baker's work. They can make it possible to obtain ready-to-bake bread-making pieces in 4 to 8 hours. They can also permit advances or the development of new techniques in the preparation and storage of bulk doughs or leavens.

Cold-sensitive bread-making yeasts make it possible to produce doughs or leavens in bulk which, once they have been cooled to a temperature below 10° C., can be stored for several days if necessary and then transported. They make it possible to carry out prefermentation in bread-making corresponding to leaven and/or first fermentation in bread-making, which occurs before division and/or shaping, in a manner that is disconnected from the overall bread-making process, and in grouped conditions, when time-consuming operations are involved. These bulk doughs can be stored in vats or boxes in cold chambers or in buckets. These applications are especially interesting in French bread-making, but they are not limited to this type of bread-making. They can be used for example for the production, and distribution in buckets, of fermented yellow doughs such as doughs for pancakes, or doughs for blini which at about 4° C. can be distributed to all the baking points.

The cold-sensitive yeasts can be used for making liquid leavens of the poolish, flour-brew and liquid sponge type, for storage for several days before use. They also make it possible, in the same way, to make dough-like leavens, such as leaven-yeasts, sponges. All these leavens can be used for making loaves, but also brioches, doughnuts, and crackers.

A particularly interesting application is to use these cold-sensitive yeasts, and preferably a fast-working, maltose-adapted cold-sensitive yeast, for making complete doughs that have undergone a long first fermentation (long pointing, to use the trade term), and then produce, with these doughs, very aromatic loaves in a maximum of 2 to 3 hours. This makes it possible in particular to return, in the case of ordinary French bread (loaves produced by kneading only flour, water, yeast and if necessary leaven, salt, without any addition of sugar or fats), to old methods with long first fermentation, and short finishing. The use of a cold-sensitive yeast, and preferably a fast-working, cold-sensitive yeast that is adapted to maltose, makes it possible to have a dough mix in bulk that has undergone long pointing, which is ready for quick production of traditional French loaves.

A novel application of cold-sensitive baker's yeasts is their use in the temperature-controlled regulation of the growth of the various microorganisms in an acid leaven containing yeasts and bacteria.

If the bread-making leaven is inoculated so that it is a mixed culture of a cold-sensitive microorganism with a high growth rate and another, psychrophilic microorganism, it is then possible to control the ratio of the two populations by defining or varying the fermentation temperature.

It is thus possible to control the production of biomass, and therefore of the metabolites produced by the biomass, and in this way promote, or not, the production of bacteria, and therefore of lactic and acetic acids.

A variant of construction of the novel strains according to the invention consists of constructing the said strains by the techniques of molecular biology, as indicated below.

A first stage can consist advantageously of revealing differences in the synthesis of soluble proteins and/or of membrane proteins of yeasts at 10° C. and 30° C. between a mutant selected as cold-sensitive and the parent strain. A mutant selected as cold-sensitive is a mutant for which fermentation is blocked or at least slowed down considerably at temperatures equal to or lower than 15° C. and is normal above 20° C., when this fermentation is measured in relation to the starting parent strain.

These comparisons can be made by the technique of two-dimensional electrophoresis of proteins with comparison of the 2-D electrophoretograms by suitable analysis software, such as the 2-D Analyzer® software, marketed in France by BIOIMAGE, 777, E. Eisenhower Parkway, Suite 950, Ann Arbor, Mich. 48108, USA. The aim of these comparisons is to detect important differences in the synthesis of proteins, and if the latter can be identified from known gene-protein indexes, such as those described in the article "Two-dimensional Protein Map of *Saccharomyces cerevisiae*: Construction of a Gene-Protein Index", which has the abbreviated title: "*S. cerevisiae* 2D protein map", of BOUCHERIE H. et al., published in "Yeast" 1995, 11(7), 601–613. If the protein is not known, it is possible in certain cases to collect it on the electrophoresis gel, determine its $NH_2$-terminal sequence, and go back to the gene that has been mutated, especially as the yeast genome is now known almost completely. Knowing the gene or genes that have undergone mutation, it is then possible by classical techniques of molecular biology to identify the mutation or mutations by cloning the mutated gene or genes, and to introduce this mutation into industrial strains.

A direct approach can also be effected by cloning the mutated gene responsible for the cold-sensitivity phenotype in the mutant that exhibits this phenotype. The results obtained suggest that the mutation responsible for the cold-sensitivity phenotype of the polyploid mutants S47-12b1, L30-13 and L30-91 is on each occasion dominant and monogenic.

A genomic DNA library is constructed for a mutant of an industrial polyploid strain, for which, preferably, the dominant and monogenic character of the mutation has been confirmed in accordance with the classical techniques of molecular biology in a centromeric vector such as the YCp50 vector, which is commonly available, and which in addition possesses the marker URA3. We then transform a ura3⁻ laboratory yeast strain, not cold-sensitive, with this DNA library and, among the URA3⁺ transformants, we look for those that have acquired the character of cold-sensitivity by the selection technique that led to the selection of cold-sensitive mutants described above, that is, the method consisting of killing the cells that have active metabolism in strict anaerobic conditions at a temperature between 10 and 15° C. It is then easy to isolate the plasmid of a transformant expressing the phenotype of cold-sensitivity, analyse the cloned yeast DNA fragment in this plasmid (restriction mapping, sequencing) to identify the gene and to reintroduce this mutated gene in an industrial yeast strain by the techniques of integration by homologous recombination in a gene that is non-essential to growth and to fermentation or in the non-mutated gene.

Other techniques of molecular biology can be employed for constructing industrial strains that have been transformed to exhibit the phenotype of cold-sensitivity of the mutants that are the object of the invention, and more especially of the S47-12b1 mutant, i.e. to obtain fast-working yeast strains expressing a phenotype of cold-sensitivity.

An interesting technique consists of causing sporulation of industrial strains, and especially strains of fast-working yeast, and applying the mutation and selection treatment described above to the segregants or haploids thus obtained. If after crossing of the segregants selected for carrying the required mutation it is verified that the mutation is dominant and monogenic, we proceed as described above for the polyploids carrying a monogenic and dominant mutation. If, on the other hand, the latter is recessive and monogenic, we then proceed as outlined below.

First we isolate a ura3⁻ clone of the segregant or haploid carrying a monogenic and recessive cold-sensitivity mutation by spreading it on a medium containing 5-fluoro-orotate or by disrupting its URA3 alleles by a positive marker or by combining these two techniques. The ura3⁻ mutant is then transformed by a genomic library of a wild-type (wt) strain such as for example the genomic DNA library constructed in the centromeric vector YCp50 and sold by ATCC under reference 37415. Then, among the URA3⁺ transformants obtained, we look for those that have lost the phenotype of cold-sensitivity, making use of their much faster metabolism in anaerobic conditions at 10° C. than the starting mutated segregants.

The wild-type gene complementing the cold-sensitivity phenotype is identified by mapping and sequencing. This identification makes it easy to isolate the mutated allele in the segregant carrying a cold-sensitivity mutation by the gene amplification technique (PCR) or by the "gap-filling" technique. The mutated allele will then be used for replacing all the wild-type copies of this gene, by homologous recombination, in the industrial strain that we wish to make cold-sensitive.

This variant is the preferred method according to the invention for obtaining mutants of interest by directed mutagenesis consisting of introducing the mutation imparting the cold-sensitivity phenotype in industrial strains of bread-making yeasts. In the context of a segregant of an industrial strain of fast-working yeast, well adapted to the fermentation of maltose, this segregant itself having this property, it has made it possible to demonstrate that a mutation on the gene YLR087c, according to the code adopted in the library resulting from the systematic sequencing of the genome of Saccharomyces cerevisiae, as synthesized and coordinated by the MIPS (Martinsried Institute for Protein Sequences—Max Planck Institute for Biochemistry—82152 Martinsried—FRG) made it possible, if all the YLR087c genes do indeed carry the mutation, to obtain industrial strains possessing the phenotype of cold-sensitivity in fermentation, regardless of their genetic context.

This result is particularly interesting for the construction of industrial strains of bread-making yeasts, and in general of industrial strains leading to fermented foods and beverages for human consumption, and especially wine or beer. This result is independent of the genetic context, since the mutation of this gene YLR087c has been identified on a strain that is well adapted to the fermentation of maltose and reintroduced, producing the phenotype in two strains that are independent of one another and of the starting strain. This mutation corresponds to a phenotype of cold-sensitivity in fermentation, with complete disappearance of the phenotype at more than 20° C. It is essential that the mutation has been identified on an industrial strain possessing a phenotype of cold-sensitivity in fermentation. Thus, the following three mutations, described in the literature as giving cold-sensitive mutants, have been studied:

the prp28-1 mutant described by STRAUSS, E. J. and GUTHRIE, C. (1991) "Genes and Development" 5, 629–641, disruption of part of the gene LTE1 (Low Temperature Essential) described by WICKNER, R. B. et al. (1987) Yeast 3, 51–57, controlled mutation of the gene BCY1 described by YAMANO, S. et al. (1987) "Mol.Gen.Genet." 210, 413–18.

The mutants prp28-1 and ltel were obtained by the authors of the publications cited above. Controlled mutation of the bcyl gene leading to a phenotype of cold-sensitivity has been reproduced in a laboratory strain. Although these three mutations lead to a phenotype of non-growth at low temperature (10° C.) on a dish of agar-agar medium as described by the authors of these works, none of these three mutants exhibited a phenotype of cold-sensitivity in conditions of fermentation in the type A fermentometer tests described. These three mutations are therefore of no interest for obtaining yeasts for bread-making, wine-making or brewing.

The invention therefore relates in particular to:

the segregant HL13.2.30 lodged with the CNCM under No. I-1841 which gives yeasts that are well adapted to maltose and possess a phenotype of cold-sensitivity in fermentation, the mutated gene such as exists in the plasmid YCp50-10.39mut in the E. coli strain DH5α lodged with the CNCM under No. I-1842, any strain of industrial yeast for bread-making, brewing, wine-making, all the YLR087c genes of which carry a non-lethal mutation conferring the phenotype of cold fermentation, and more generally all the industrial yeasts for bread-making, wine-making and brewing whose genes coding for membrane proteins that have a function comparable to that of the YLR087c gene or the genes coding for proteins associated with the protein encoded by the YLR087c gene or the genes coding for proteins having similarities of sequence, i.e. at least 50% homology, carrying a non-lethal mutation conferring the phenotype of cold fermentation.

Finally it is possible to obtain industrial strains, especially fast-working and very fast-working strains, possessing cold-sensitivity as defined within the scope of the present invention, by causing the expression in this strain, in a conditional manner, i.e. only at low temperature (0 to 15° C. or 20° C.), of a gene whose expression results in a very sharp decrease in fermentation activity of the strain in question.

Genes or mutated alleles of genes whose expression leads to a very sharp decrease in assimilation of sugars by the yeast and/or a considerable lowering of its fermentation activity, have been described in the literature. Expression of one of these genes (or mutated alleles), dependent on a temperature-controlled promoter leading to strong expression of the gene at low temperature and almost zero expression of the gene above 20° C., such as the promoters of genes coding for "cold shock" proteins, several of which have been described, is a means of directly constructing a cold-sensitive yeast strain, starting from the most powerful industrial strains.

Conditional promoters are for example promoters of the TIP1 gene or of genes that are homologues of TIP1 or their mutated alleles, described in particular in the article "Identification of cis- and trans-acting elements involved in the expression of cold shock inducible TIP1 gene of Yeast *Saccharomyces cerevisiae*", by MUNOS-DORADO J. et al., published in "Nucleic Acid Research", 1994, Vol. 22, No. 4, 560–568, or in the article "Cold shock induction of a family of TIP1 related proteins associated with the membrane in *Saccharomyces cerevisiae*", by KOWALSKI, L. et al., published in "Molecular Microbiology" 15, No. 2 (January 1995), 341–353. These promoters, which are conditional as a function of temperature, like those of the family of the promoter of the TIP1 gene, can also be combined with a gene coding for a transcription regulating factor having an action of the repressor type, for example the gene MIG1. This gene MIG1 codes for a zinc finger protein which is involved in the principal route of glucose repression and blocks the transcription of genes which have in their promoter a URS (Upstream Regulatory Sequence) consensus sequence, as described in the article by NEHLIN, J. O. and RONNE H., published in EMBO J. 1990, 9, 2891–2898 with the title "Yeast MIG1 repression is related to the mammalian early growth response and Wilm's tumour finger proteins". To complete the construction, a consensus sequence, recognized by the protein encoded by the repressor gene that is made dependent on a conditional promoter, is inserted in the promoter of a gene that is essential for fermentation. For example, the consensus sequence recognized by the protein encoded by the gene MIG1 described in the article of NEHLIN et al. cited above, is incorporated in the promoters of all the alleles of the pyruvate kinase gene.

We can also look for conditional expression of a gene that is essential to the fermentation of yeasts, for example a glycolysis gene such as the genes coding for pyruvate kinase or pyruvate decarboxylase. This condition expression can be brought about by cloning this gene under the dependence of a promoter whose expression is almost zero below 15° C. and is normal at 30° C. An interesting alternative method of obtaining conditional expression of a gene is that described in the article "Control of gene expression by artificial introns in *Saccharomyces cerevisiae*", by YOSHIMATSU T. and VAGANA F., published in "Science" 1988, 244 (4910), 1346–1348, all the documents cited in the present description of the invention being incorporated by reference.

The invention is illustrated by the following examples:

EXAMPLE 1

Production and Selection of Mutants

Commercial strains of bread-making yeast, especially strains of compressed yeasts marketed in Europe, and more particularly the strains used for the production of fast-working compressed yeasts intended for bread-making of the French type, with little or no added sugar, are selected.

They are to be submitted to the following mutation treatment:

Cells collected in the stationary phase are mutagenized with ethyl methyl sulphonate (EMS) so as to obtain 10 to 20% survival. The mutagenized cells are then regenerated by rich-medium culture: YPG for 3 h at 30° C. and then incubated in conditions of strict anaerobic fermentation for 48 h at 10° C. (YPG). Then add nystatin or any agent that is an inhibitor of dividing cells, and incubate again for 2 h at 10° C.

The post-mutagenesis enrichment treatment can be repeated advantageously 2 to 3 times. The nystatin concentration is adjusted to obtain a survival rate of 0.01%. Spread out the cell suspension resulting from nystatin enrichment at a suitable dilution to obtain isolated colonies of the mutants obtained.

The mutants thus obtained are selected by measuring the sugars consumed, in relation to the unmutated starting strain.

The mutants are cultivated on YEG-AGAR medium for 24 hours. The yeasts are collected and the yeast cells are suspended in distilled water, in such a way that this suspension has an optical density of 15.

10 microliters of this yeast suspension is incubated in the presence of 100 microliters of YPM and YPG/M culture medium on a microtitration plate.

The microtitration plates are incubated either for 8 hours at 30° C., or for 60 hours at 10° C.

At the end of the incubation time, fermentation of the sugar or sugars is blocked by adding sodium dinitrosalicylate reagent, which serves for assaying the reducing sugars by colorimetric reaction after heating the microtitration plate at 55° C. for 30 minutes.

Select the mutants which, on the one hand, after 60 hours at 10° C. have fermented at most about 60% of the glucose/maltose mixture of the YPG/M medium and at most 30% of the maltose of the YPM medium relative to the sugars fermented by the unmutated starting strain and which on the other hand, at 30° C. for 8 hours, have consumed at least 90% of the sugars consumed by the unmutated starting strain.

By measuring the consumption of sugar or sugars at low temperature in this way, it is possible to quantify the character of cold-sensitivity of the strains and eliminate the mutants with slight cold-sensitivity. An initial elimination can be done by eye. The strains whose fermentation is slowed down at 10° C. give a dark brown coloration, the mutated strains that have low sensitivity give an orange coloration, indicating a low proportion of residual reducing sugars. This initial selection by visual examination provides an initial sorting, which is then supplemented with measurements of sugar consumption.

By measuring the consumption of sugar or sugars at 30° C., we can eliminate the mutants whose fermentation is affected overall, whatever the temperature.

Next, the performance of the selected strains is verified by culture tests. It is possible to carry out semi-anaerobic laboratory tests, giving a sufficient harvest to permit measurements of fermentation activity according to the test series A described above. It is also possible to carry out aerobic cultures in reduced volume, which is then gradually increased.

Verify that the mutants are stable and can be multiplied in conditions that are equivalent and with yields that are equivalent to the unmutated starting strain, which is a strain that is used industrially for the production of bread-making yeasts.

Within the framework of this example, three strains were selected in particular:

strain S47-12b1, a stable mutant of a strain of fast-working yeast commonly used in Europe for the production of compressed fresh yeasts, this stable mutant S47-12b1 was lodged with the CNCM under No. I-1645 on May 12, 1995;

strains L30-13 and L30-91, stable mutants of a yeast strain commonly used in Europe for the production of compressed fresh yeasts for sugar-containing dough. These stable mutants were lodged with the CNCM, mutant L30-13 under No. I-1647, mutant L30-91 under No. I-1646, both being lodged on May 12, 1995.

These three strains gave the following results in selection tests of sugar consumption for 60 h at 10° C. on microtitration plates, the optical density being read with a type Metertech $\Sigma_{960}$® plate reader, Micro Elisa Autoreader in the conditions described above:

B vitamins) are present at least in the largest amounts recommended in the reference works cited above. In general, these tests are carried out as indicated in the Applicant's previous patents, such as European patent application No. 92401168.7 of Apr. 23, 1992. In particular, make sure that the yeasts obtained are washed well, with rapid cooling of the cream, the yeasts being filtered at 2° C.

The last stage of multiplication of the yeast, leading to a very active compressed fresh yeast, is carried out more specifically in the following way:

dilution of the culture medium at the end of commercial multiplication:

$$\frac{\text{Weight of yeast} - \text{containing wort in the vat}}{\text{Quantity of molasses at 50\% total sugars expressed as sucrose}} = 5.2$$

Preferably, these tests are carried out with a mixture of 90% of beet molasses and 10% of cane molasses, and both molasses must be of good quality, i.e. of good purity and

| Medium | Commercial strain S47 fast-working yeast | Mutant S47-12b1 | Commercial strain yeast for suger-containing dough L30 | Mutant L30-13 | Mutant L30-91 |
|---|---|---|---|---|---|
| | 60 hours at 10° C. | | | | |
| YP maltose | | | | | |
| OD: 2.25 | 0.102 | 2.02 | 0.13 | 1.71 | 2.00 |
| % sugar consumed | 95.5% | 9.8% | 94% | 24% | 11% |
| YP maltose/glucose | | | | | |
| OD: 2.63 | 0.135 | 1.19 | 0.21 | 1.13 | 1.70 |
| % sugar consumed | 95% | 55% | 92% | 57% | 35% |
| | 8 hours at 30° C. | | | | |
| YP maltose | | | | | |
| OD: 2.25 | 0.15 | 0.18 | 0.183 | 0.22 | 0.25 |
| % sugar consumed | 93% | 92% | 92% | 91% | 89% |
| YP maltose/glucose | | | | | |
| OD: 2.63 | 0.12 | 0.155 | 0.17 | 0.205 | 0.23 |
| % sugar consumed | 95% | 94% | 93% | 92% | 91% |

EXAMPLE 2

Culture of the Three Mutants Selected According to Example 1

The three stable mutants S47-12b1, L30-13 and L30-91 were cultivated in the following manner.

Apart from the use of methods and equipment specified below, the strains were propagated in several stages of aerobic multiplication, the fresh yeast was harvested, washed, filtered using conventional equipment employed in yeast production and according to the usual production methods, such as the equipment and methods described in the work "Yeast Technology" of Gerald Reed and Henry J. Peppler (1973), The Avi Publishing Company Inc. or in the chapter "Production of Baker's Yeast", Gerald Reed, published by Prescott and Dunn's Industrial Microbiology, 4th edition, edited by Gerald Reed, The Avi Publishing Co. Inc., second printing 1983.

Particular attention is paid to ensuring that all the nutrients required by yeast in small amounts, minerals (macroelements and trace elements), vitamins (biotin, group must not contain inhibitors or substances that are toxic to the yeasts. It is necessary in particular to verify by tests with control cultures that the molasses do not contain toxic additives, which are sometimes added during the operations of extraction and purification of sugar in the refinery. The sugar of the beet molasses is measured by the Clerget method (determination of sucrose by double polarization), the sugar of the cane molasses is determined by enzymatic measurement of sucrose, glucose and fructose actually present, and the total of these sugars is calculated in sucrose equivalent;

mean hourly rate of multiplication for the last cycle of multiplication of 14 hours: 1.12 to 1.14 maximum proportion of buds of the harvested yeast: 3% nitrogen/dry matter ratio, harvested yeast: 7%

$P_2O_5$/dry matter ratio, harvested yeast: 2.5%.

These tests gave fresh bread-making yeasts with about 32% of dry matter, with the following characteristics. All the results given in the tables are for fresh yeasts adjusted to 32% of dry matter.

Measurements at 30° C.

| Strain | Culture yield on molasse equivalent at 50% sucrose | Test $A_1$ 2h 30° C. | Test $A_3$ 2h 30° C. | in ml de $CO_2$ Test $A_5$ 2h 30° C. | Test $A_6$ 2h 30° C. |
|---|---|---|---|---|---|
| strain S47 | 90% | 140 | 120 | 90 | |
| strain S47-12b1 | 88% | 115 | 97 | 65 | |
| strain L30 | 82% | 88 | 125 | 110 | 165 |
| strain L30-13 | 87% | 88 | 120 | 103 | 145 |
| strain L30-91 | 82% | 70 | 117 | 98 | 135 |

Measurements at 8° C. with Temperature Rise

| Strain | Test | 48 h 8° C. | rise to 30° C. for 1 h 30 | 30° 1 h | Total 30° C. 2 h |
|---|---|---|---|---|---|
| S47 | $A_1$ | 167 | 34 | 12 | 18 |
| S47-12b1 | $A_1$ | 44 | 48 | 54 | 118 |
| S47 | $A_5$ | 171 | 81 | 69 | 135 |
| S47-12b1 | $A_5$ | 13 | 42 | 35 | 76 |
| L30 | $A_1$ | 121 | 36 | 18 | 30 |
| L30-13 | $A_1$ | 12 | 50 | 47 | 100 |
| L30-91 | $A_1$ | 2 | 42 | 24 | 43 |
| L30 | $A_5$ | 174 | 68 | 66 | 127 |
| L30-13 | $A_5$ | 6 | 36 | 44 | 99 |
| L30-91 | $A_5$ | 1 | 23 | 47 | 98 |

From the above tables, we can calculate the ratio:

$$\frac{\text{release of } CO_2 \text{ after 48 hours of fermentation at } 8° C.}{\text{release of } CO_2 \text{ after 2 hours of fermentation at } 30° C.} \text{ in \%}$$

The following table is obtained:

| Strain | Ratio in test $A_1$ | Ratio in test $A_5$ |
|---|---|---|
| S47 | 119% | 190% |
| S47-12b1 | 44 ÷ 115 = 38% | ≈20% |
| L30 | 138% | >158% |
| L30-13 | 14% | 6% |
| L30-91 | 3% | 1% |

The fresh bread-making yeasts obtained in the whole of this example are stable in a storage test for 7 days at 21° C.

EXAMPLE 3

Culture of the Stable Mutant S47-12b1 at About 8% Nitrogen Relative to Dry Matter The stable strain S47-12b1 and the control strain S47 are cultivated in the same conditions as in example 2, except that:

mean hourly rate of multiplication in the last cycle of multiplication of 14 hours: 1.18 maximum proportion of buds of the harvested yeast: 5% nitrogen/dry matter ratio, harvested yeast: 8.2%

$P_2O_5$/dry matter ratio, harvested yeast: 2.7%.

The following results are obtained:

Measurements at 30° C.

| Strain | Culture yield on molasse equivalent at 50% sucrose | Test $A_1$ 2h 30° C. | Test $A_3$ 2h 30° C. | in ml of $CO_2$ Test $A_5$ 2h 30° C. |
|---|---|---|---|---|
| strain S47 | 91% | 170 | 155 | 105 |
| strain S47-12b1 | 91% | 172 | 149 | 103 |

Measurements at 8° C. with Temperature Rise

| Strain | Test | 48 h 8° C. | rise at 30° C. for | 30° C. in ml de $CO_2$ 1 h | 2 h | 3 h |
|---|---|---|---|---|---|---|
| S47 | $A_1$ | 195 | 32 | 10 | 8 | 2 |
| S47 | $A_5$ | 190 | 65 | 65 | 70 | 50 |
| S47-12b1 | $A_1$ | 66 | 50 | 62 | 53 | 11 |
| A47-12b1 | $A_5$ | 8 | 36 | 40 | 42 | 48 |

It is then possible to calculate the ratios of $CO_2$ release in tests $A_1$ and $A_5$:

| $\frac{\text{release of } CO_2 \text{ after 48 hours of fermentation at } 8° C.}{\text{release of } CO_2 \text{ after 2 hours of fermentation at } 30° C.}$ | | |
|---|---|---|
| S47 | test $A_1$ | 115% |
| | test $A_5$ | 110% |
| S47-12b1 | test $A_1$ | 66 ÷ 172 = 38.4% |
| | test $A_5$ | 8 ÷ 103 = 8% |

The fresh bread-making yeasts obtained with these two strains are stable in the same way in a test of storage for 7 days at 21° C.

EXAMPLE 4

Isolation of a Mutated Gene Responsible for the Phenotype of Cold-Sensitivity in the Context of a Fast-Working, Maltose-Adapted Strain, and Cloning of this Gene in Yeast Strains Sporulation is induced, by the usual techniques, in industrial strains of fast-working yeast, adapted to maltose, for example the strain NCYC 995, the object of U.S. Pat. No. 4 396 632 of Aug. 2, 1983 in the names of Philippe Clement and Annie Lolez. In this way a certain number of haploids is obtained, including the haploid or segregant designated with the No. HL13.2. The haploids thus obtained are submitted to the treatment of mutation and selection of mutants described in example 1. In this way, the cold-sensitive haploid strain designated HL13.2.30 is selected. This industrial haploid mutant HL13.2.30 is characterized by the fact that after culture, it can be used for obtaining a yeast that has the following characteristics:

test $A_1$ 2 hours at 30° C.: 132 ml of $CO_2$ $$\frac{\text{release of } CO_2 \text{ in the } A_1 \text{ after 48 hours at 8° C.}}{\text{release of } CO_2 \text{ in test } A_1 \text{ after 2 hours at 30° C.}} = 0.35$$

This haploid mutant exhibits, according to these results, good adaptation to maltose owing to its activity which is above 100 in test $A_1$ and a character of cold-sensitivity in view of the ratio calculated above of 0.35. The study by crossing of the cold-sensitivity of this mutant HL13.2.30 shows that a mutation is involved, as it can be transmitted and it is recessive. The phenotype conferred by this mutation does not depend a priori on the genetic context of the strain.

In view of these results, cloning of the gene responsible for the phenotype of cold-sensitivity of this mutated haploid strain with the designation HL13.2.30 was undertaken according to the following general strategy, each stage of which will be discussed again in more detail later on. The mutated haploid strain HL13.2.30 was lodged with the CNCM, Pasteur Institute, Paris, under No. I-1841 on Jan. 30, 1997.

1) General strategy

Isolation of a mutant ura3⁻ of strain HL13.2.30 so as to be able to transform it with the genomic DNA library reference ATCC 37415 constructed in the centromeric vector YCp50 (marker URA3). [ROSE, M. D. et al. (1987) Gene 60, 237–243].

Transformation of a mutant HL13.2.30 ura3⁻ by the genomic DNA library and isolation of clones that have become URA3⁺ (clones that have received a plasmid).

Search for transformant clones that have lost the phenotype of cold-sensitivity.

Verification of the clones that have lost the phenotype of cold-sensitivity.

Isolation and characterization of the plasmid after re-isolation of the latter from a transformant that has lost the character of cold-sensitivity.

Retransformation of the strain HL13.2.30 ura3⁻ with the re-isolated plasmid and verification that it complements the mutation effectively.

Chromosomic localization of the genomic DNA fragment inserted in the plasmid by sequencing of the 3' and 5' ends of the insert.

Identification of the ORF (open reading frame) responsible for removal of the character of cold-sensitivity.

Isolation of the gene carrying the mutation from the HL13.2.30 mutant.

Sequencing of the mutated gene and of its "wt" (wild type) allele of strain HL13.2 for identification and localization of the mutation.

Retransformation of the strain HL13.2.30 ura3⁻ (mutant) with the mutated gene so as to verify that it is not a suppressor gene.

Reintroduction (by homologous recombination) of the mutated gene in a segregant that is not cold-sensitive (laboratory strain n=16 chromosomes), verification that the phenotype of cold-sensitivity has been obtained and demonstration of monogenicity and of non-dependence on the genetic context of the original mutated strain.

All the constructions were effected by the usual techniques and especially according to the work "MOLECULAR CLONING", J. Sambrook, E. F. Fritsch, T. Maniatis, Cold Spring Harbor Laboratory Press 1989.

2) Isolation of a mutant ura3⁻ of strain HL13.2.30

This stage was necessary so as to be able to transform strain HL13.2.30 by the genomic library and select the transformants that have become URA⁺ by introduction of the plasmid.

The route taken so that the HL13.2.30 strain can be made ura3⁻ is disruption of the URA3 alleles of this strain by the phleomycin resistance gene. A cassette was constructed for disruption of the URA3 gene by phleomycin in the plasmid YIp lac 211 (URA3) [GIETZ, R. D. and SUGINO, A. (1988) Gene 74, 527–534].

The construction (shown diagrammatically in FIG. 1) comprises the following steps:

preparation of the fragment pTEF1/Tn5 Ble/t CYC1 (phleomycin resistance gene) by double hydrolysis Hind III/Kpn I of plasmid pUT332 [GATIGNOL, A. et al. (1987) "Mol. Gen. Genet." 207, 342–348]. The fragment is recovered on LMP (low melting point) agarose gel, purified with the QIAEX kit (sold by QIAGEN) and made blunt-ended by T4 DNA Polymerase.

opening of the plasmid YIp lac 211 by the enzyme Stu I which cuts inside the URA3 gene (single site) and generates blunt ends. The open plasmid is then dephosphorylated by CIP (Calf Intestine Phosphatase) to prevent recircularization of the plasmid during cloning.

cloning of the blunt-ended fragment pTEF1/Tn5 Ble/t CYC1 in the plasmid YIp lac 211—Stu I—dephosphorylated by the action of T4 DNA ligase.

transformation of the *E. coli* strain DH5α (sold by LIFE TECHNOLOGIES) by the preceding ligate and isolation of clones that have incorporated the phleomycin resistance gene.

liberation of the ura3::PHR disruption cassette (URA3 gene disrupted by the phleomycin resistance gene) by Nde I/Nsi I double hydrolysis, obtaining liberation of a fragment of 2.1 kb=ura3::PH$^R$.

The HL13.2.30 strain was transformed by electroporation with the fragment ura3::PH$^R$ of 2.1 kb (1 μg). Several PH$^R$ clones were obtained but they were all still URA⁺ thus demonstrating the existence of a second URA3 allele (at least) in the HL13.2.30 strain.

A second disruption was effected with the same DNA cassette but this time selection was effected on a minimum medium+uracil+5FOA (5-fluoro-orotate), a medium that permits direct selection of ura3⁻ clones: several FOA⁺ clones were obtained, they were all ura3⁻. The HL13.2.30 strain therefore contains two copies of the URA3 gene.

3) Transformation of the HL13.2.30 ura3⁻ strain by the genomic library

Several transformations of the HL13.2.30 ura3⁻ strain were effected with the plasmid DNA of the ATCC 37415 genomic library constructed in the centromeric vector YCp50. The transformations were effected by the lithium acetate technique: $10^8$ cells/transformation in the presence of 600 ng of DNA (as described by GIETZ, D. et al. (1992) "Nucl. Acids Res." 20, 1425).

More than 5000 transforming clones were obtained, 4500 of which were screened in a preselection test consisting of a drop test on a 0.1% glucose medium preferably with antimycin (5 µg/ml).

The transformants are cultivated on minimum medium YNB-agar DIFCO® containing 2% glucose for 24 hours. The yeasts harvested are suspended in distilled water; the suspension is adjusted to an optical density of 1. 5-microliter drops of this suspension are deposited on minimum medium YNB-agar DIFCO® containing 0.1% glucose and 5 µg/ml of antimycin A (reference A 8674 in the SIGMA catalogue), antimycin A being a respiration blocking agent. The dishes containing this minimum medium and thus inoculated are incubated at 10° C. for 10 days. The transformants that have multiplied owing to the energy produced by fermentation are selected, since their respiration is blocked by the antimycin A, more quickly than the starting mutant HL13.2.30 ura3⁻ transformed by the empty plasmid YCp50, i.e. without insert.

This preselection made it possible to find about fifty clones exhibiting improved growth at 10° C. relative to the control, i.e. displaying reversion to the wild-type phenotype. All these clones were submitted to a more detailed study to see whether, among these candidates, a clone had effectively lost its character of cold-sensitivity by transformation with the library.

The additional tests that were carried out on these clones are as follows:

Glucose test at 10° C.: measurement of the consumption of glucose at 10° C. in fermentation conditions compared with controls HL13.2.30 ura3⁻/YCp 50 (cold-sensitive mutant) and HL13.2 (wild-type strain) so as to verify the presence or absence of the phenotype of cold-sensitivity in fermentation, this test having been correlated with type A tests with the Burrows and Harrison fermentometer as described above.

The description of the glucose test is as follows: the various clones are cultivated on a minimum medium for 24 h. The yeasts are harvested and the yeast cells are suspended in distilled water, in such a way that this suspension has an optical density of 15. 10 microliters of this yeast suspension is incubated in the presence of 100 microliters of minimum medium (yeast nitrogen base, w/o Amino-acid DIFCO® containing 0.02% glucose, on a microtitration plate. The microtitration plates are incubated either at 30° C. for 4 h, or at 10° C. for 20 h. At the end of the incubation time, the glucose that has not been fermented by the yeasts is detected by a calorimetric reaction, with glucose oxidase (Diagnostic Kits Sigma No. 315-100). This test is a variant of the microtitration plate test with detection of the consumption of sugar with sodium dinitrosalicylate described in example 1.

Fermentometer 48 h at 8° C. according to test $A_1$ so as to verify loss of the character of cold-sensitivity.

Identification of the clones by a technique of PCR fingerprinting (Ness et al., 1993, "J.Sci.Food Agric.", 62, 89–94) so as to verify that contaminants are not involved.

Growth on medium YEG-Agar+phleomycin 100 µg/ml to check for presence of the character of phleomycin resistance supplied during disruption of the URA3 alleles of the HL13.2.30 strain.

Verification of the presence of a plasmid: isolation of the total DNA and retransformation of the E. coli strain DH5α to isolate the plasmid.

Among the fifty or so clones registered by the drop test, a clone that satisfied all these tests was found: clone YCp50-10.39. This clone was submitted to complete characterization.

4) Investigation of clone YCp50-10.39
  a) Confirmation of loss of the phenotype of cold-sensitivity by the transformation So as to verify that loss of the character of cold-sensitivity was indeed connected with the presence of a genomic DNA fragment supplied by the plasmid, we compared, in the fermentometer at 8° C., the releases of gas from the following strains:

HL13.2: control

HL13.2.30 ura3⁻ [YCp50]: control yeast, cold-sensitive (strain transformed by the "empty" plasmid).

HL13.2.30 ura3⁻[YCp50-10.39]: clone YCp50-10.39 isolated after transformation of strain HL13.2.30 ura3⁻ (cold-sensitive yeast) by the genomic DNA library.

HL13.2.30 ura3-[YCp50-10.39 RT]: clone isolated after retransformation of strain HL13.2.30 ura3⁻ by the plasmid isolated from the original clone YCp50-10.39.

HL13.2.30 ura3⁻[YCp50-10.39 FOA]: clone isolated on 5-FOA (ura⁻) after loss of the plasmid on rich medium of the original YCp50-10.39 clone.

Measurements of releases of gas ($CO_2$) in the Burrows and Harrison fermentometer in test $A_1$ at 8° C. for 24 or 48 hours show:

that the three strains HL13.2, HL13.2.30 ura3⁻ [YCp50-10.39] and HL13.2.30 ura3⁻ [YCp50-10.39RT] give $CO_2$ release of the same order of magnitude, and therefore like strain HL13.2 do not exhibit any phenotype of cold-sensitivity whereas the two strains HL13.2.30 ura3⁻ [YCp50] and HL13.2.30 ura3⁻ [YCp50-10.39FOA] both give $CO_2$ release that is about 3 times less than that of the group formed by the above 3 strains, these two strains therefore exhibit a phenotype of cold-sensitivity.

These results, verified several times and on several separate clones, show unambiguously that the character of cold-sensitivity of the HL13.2.30 ura3⁻ strain is complemented in the YCp50-10.39 clone and that the complementation is certainly connected with the presence of the recombinant plasmid.

b) Isolation and characterization of the plasmid present in the YCp50-10.39 clone The plasmid of the transforming clone YCp50-10.39 was isolated after transformation of the E. coli strain DH5α with the total DNA of the YCp50-10.39 clone prepared by the QIAGEN kit.

Basic mapping of the plasmid showed that:

the plasmid certainly did contain an insert, the size of the insert was greater than 15 kb.

The 5' and 3' ends of the insert were sequenced in order to locate this genomic DNA fragment in the genome of Saccharomyces cerevisiae. The sequence obtained made it possible to determine, by consulting, on the INTERNET, the data bank of the MIPS (Martinsried Institute for Protein Sequences—Max Planck Institute for Biochemistry—82152 Martinsried—FRG) at the Internet address: http://speedy.mips.biochem.mpg.de/mips/yeast/index.htmlx, that:

the insert corresponded to a DNA fragment of chromosome XII, the exact size of the insert is 18178 bp, the DNA fragment is aligned on chromosome XII (to the right of centromere) at the level of the nucleotides 305116 to 323293.

The insert comprises the following 5 complete open reading frames, numbered below with Roman numerals from I to V:

I: YLR087c
  ORF of 8874 bp (base pairs) corresponding to a protein of 2958 AA (amino acids)
  a protein called "hypothetical", in that it has never been isolated—no known homology or similarity
  4 transmembrane zones
II: YLR088w
  ORF of 1842 bp: protein of 614 AA
  known gene: GAA1 (=END2) coding for a protein involved in the translocation of the GPI anchors (N—glucosyl phosphatidyl inositol) on the proteins attached to the membrane by these anchors
  disruption of this gene is lethal
III: YLR089c
  ORF of 1776 bp: protein of 592 AA
  protein having a strong homology with alanine transaminases
IV: YLR090w
  ORF of 1377 bp: protein of 459 AA
  protein that has homologies with the Dna J protein (=heat shock protein in *E. coli*)
  expression not demonstrated in *S. cerevisiae* could be a cryptic gene
  deletion of the viable gene: no phenotype
V: YLR091w
  ORF of 879 bp: protein of 293 AA
  hypothetical protein. No known homology.

This notation YLR087c for the first ORF corresponds to the following code in the data bank:
Y=Yeast=the yeast *Saccharomyces cerevisiae*
L=Chromosome XII
R=to the right of the centromere
087=ORF No. 087
c=protein encoded by the Crick strand c) Identification of the gene responsible for removal of the character of cold-sensitivity For precise identification of the gene responsible for complementation of the character of cold-sensitivity of strain HL13.2.30 ura3⁻, we effected various sub-clonings and deletions to arrive at the result.

the deletions were effected directly starting from the plasmid YCp50-10.39 sub-clonings of fragments of the insert of 18178 bp were effected in plasmid YCp lac33 [GIETZ, R. D. and SUGINO, A (1988) Gene 74, 527–534].

Figure 2:
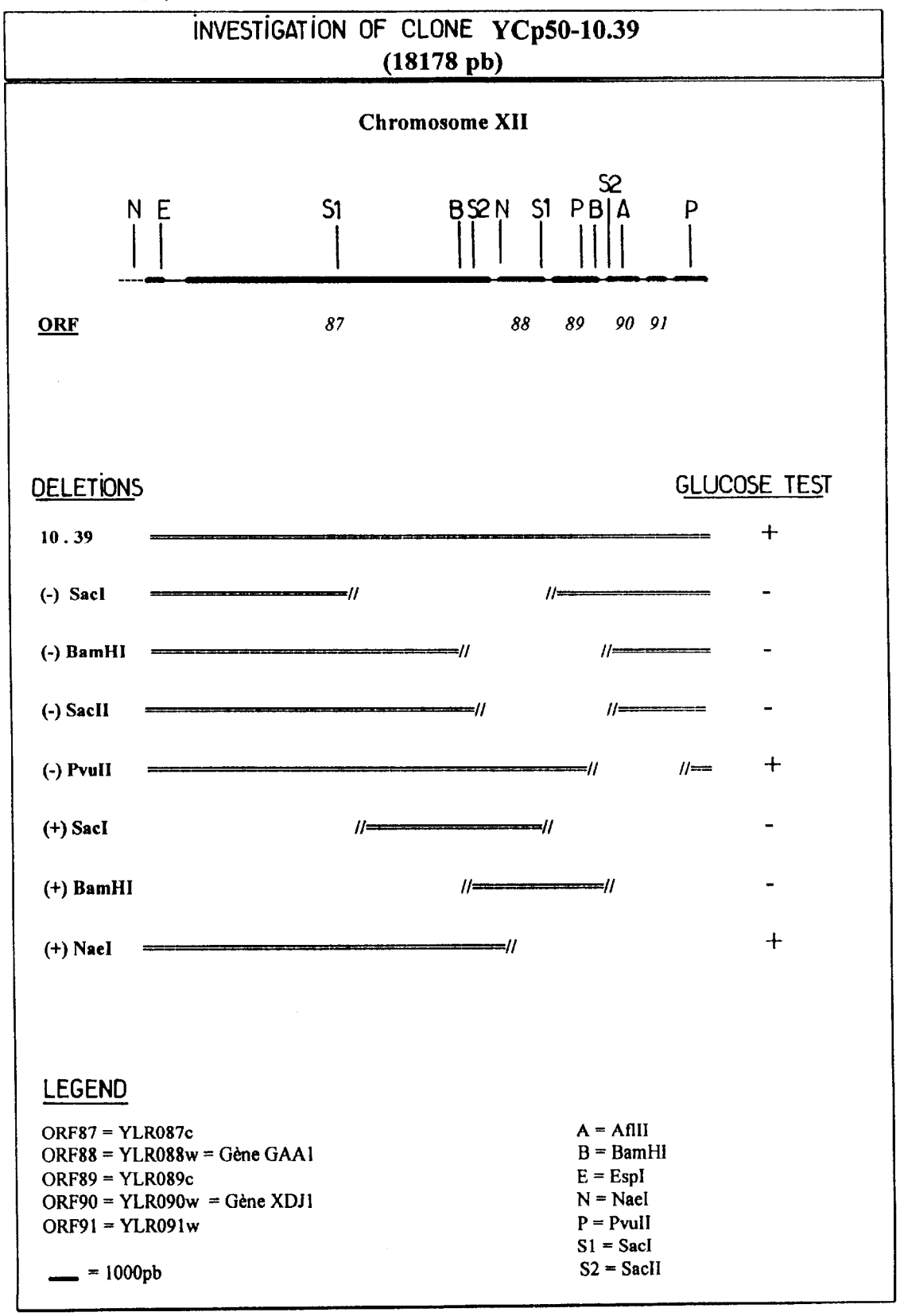
FIG. 2 is a diagrammatic representation of the investigation of clone YCp50-10.39 (18178 pb)

The strategy adopted is presented in FIG. 2 with the results obtained with the glucose test ("+": complementation of the character of cold-sensitivity; "−": non-complementation). These results were confirmed by measurements of gas release in the fermentometer after 24 or 48 h at 8° C. according to test $A_1$.

HL13.2: control, not cold-sensitive.
HL13.2.30 ura3⁻[YCp50-10.39]: clone YCp50-10.39 isolated after transformation of strain HL13.2.30 ura3⁻ (cold-sensitive) by the genomic DNA library.
HL13.2.30 ura3⁻[YCp lac33-YLR087c]: strain HL13.2.30 ura3⁻ transformed by plasmid YCp lac33 in which the wild-type gene YLR087c has been cloned (fragment NaeI—NaeI of the plasmid of YCp50.10.39).
HL13.2.30 ura3⁻[YCp50-10.39mut]: strain HL13.2.30 ura3⁻ transformed by the plasmid [YCp50-10.39mut] obtained by the gap-filling technique described in paragraph d) below. This plasmid contains the gene YLR087c carrying the mutation.
HL13.2.30 ura3⁻[YCp50]: strain HL13.2.30 ura3⁻ transformed by the "empty" plasmid YCp50 (original plasmid of the ATCC genome library).
HL13.2.30 ura3⁻[YCp lac33]: strain HL13.2.30 ura3⁻ transformed by the "empty" plasmid YCp lac33 (centromeric plasmid URA3 used for the various sub-clonings).

Releases in the fermentometer at 8° C. according to test $A_1$ from these various strains gave the following results:
the three strains HL13.2, HL13.2.30 ura3⁻[YCp50-10.39], HL13.2.30 ura3⁻[YCp lac33-YLR087c] give release of $CO_2$ gas that is of the same order of magnitude and therefore, like the control strain HL13.2, do not exhibit any phenotype of cold-sensitivity;

on the other hand, the three strains HL13.2.30 ura3⁻[YCp50-10.39mut], HL13.2.30 ura3⁻[YCp50] and HL13.2.30 ura3⁻[YCp lac33] give a release of $CO_2$ gas that is about 3 times less than the preceding group and therefore exhibit a phenotype of cold-sensitivity.

From the results of the glucose test and the fermentometer at 8° C., it is clear that the gene responsible for complementation is the gene YLR087c, coding for a protein of 2958 AA (amino acids), of completely unknown function and probably located in the membrane.

d) Isolation of the mutated gene YLR087c

In order to verify that it was indeed the required gene, responsible for the phenotype, and not a suppressor gene, we cloned the mutated gene of the strain HL13.2.30 ura3⁻ by the gap-filling technique [IWASAKI, T. et al. (1991) Gene 109, 81–87] or "allele rescue" technique [ORR-WEAVER, T. L. et al. (1983) "Methods Enzymol." 101, 228–245]. The principle of the method is given more particularly in FIG. 2 "Basic strategy for cloning GAP regions", page 83 of the article by IWASAKI, T. et al.

This method was applied to the strain HL13.2.30 ura3⁻, transforming it with the plasmid YCp50-10.39 D Sac I (cf. FIG. 2) digested by Esp I and Afl II. Use of a plasmid with deleted insert (by Sac I) is necessary to verify that filling has indeed occurred (and it is not incomplete hydrolysis of the plasmid). Three clones corresponding to the expected result (called GF2, GF4 and GF5) were obtained.

Retransformation of strain HL13.2.30 ura3⁻ with the DNA isolated from clone GF2 (=YCp50-10.39 mut.) showed that the URA⁺ transformants obtained were all cold-sensitive.

This result demonstrates that the gene YLR087c is not a suppressor gene of the character of cold-sensitivity of strain HL13.2.30 ura3⁻. In fact, if YLR087c were a suppressor gene (and therefore not mutated), its episomic expression after transformation of strain HL13.2.30 ura3⁻ by the DNA of GF2 would have led to removal of the character of cold-sensitivity.

The plasmid YCp50-10.39mut in the *Escherichia coli* strain DH5α was lodged with the CNCM (National Collection of Cultures of Microorganisms), Pasteur Institute, under No. I-1842 on Jan. 30, 1997.

e) Determination of the nucleotide sequence of the mutated gene YLR087c—Identification of the mutation:

The YLR087c gene of strain HL13.2.30 (lodged at the CNCM under number I-1841) was sequenced completely by the technique of direct sequencing on PCR products obtained by amplification of fragments of about 1 kb covering the whole gene. All the PCR fragments sequenced overlap, so there is no longer any unsequenced zone of the gene. The sequence was determined starting from the ends of the ORFs YLR086w and YLR088w contiguous with the YLR087c gene.

The sequence obtained was compared with the sequence of the YLR087c gene published in databases and which can be obtained from the MIPS (Martinsried Institute for Protein Sequences—Max Planck Institute for Biochemistry—82152 Martinsried—FRG) and especially the Internet site: http://speedy.mips.biochem.mpg.de/mips/yeast/index.htmlx.

By comparing the sequences it was possible to identify 35 changes (or non-determinations) of nucleotides in the coding region of the gene:

27 changes (or non-determinations) not inducing any change of the amino acid in the polypeptide chain 7 changes inducing alteration of the amino acid 1 change causing appearance of a STOP codon (position No. 7865 of the gene—sequence SEQ ID No. 1, this position corresponds to position No. 308242 in chromosome XII in the MIPS sequence).

To verify whether or not these were true mutations, the YLR087c gene of strain HL13.2 (wild-type strain from which the HL13.2.30 mutant was obtained) was sequenced according to the same strategy in the regions where changes had been identified.

All the aforementioned changes were found in the sequence of the wild-type gene except the change identified at position No. 7865 (C→G] leading to the change Ser→STOP (TCA→TGA).

This change, which corresponds to a true mutation of the YLR087c gene of strain HL13.2.30 (since it is not found in the sequence of the wild-type gene), causes stoppage of translation of the protein encoded by this gene, giving rise to synthesis of a truncated protein of 2496 AA in the mutant whereas the normal protein synthesized by a wild-type strain is made up of 2958 AA (amino acids).

The plasmid DNA of clones [YCp50-10.39] and [YCp50-10.39mut] was also sequenced on 120 bp (double-strand sequencing on plasmid DNA) in the region of the insert covering the STOP codon. The result obtained confirmed the existence of the mutation identified on the genomic DNA. The sequence read (position 7864→7866 in sequence SEQ ID No. 1) is:

TCA (Ser) for clone [YCp50-10.39]
TGA (STOP) for clone [YCp50-10.39mut]

The clone DH5α[YCp50-10.39mut] containing the plasmid that in turn contains the mutated gene YLR087c lodged with the CNCM under No. I-1842, therefore effectively includes this mutation.

The sequence of the mutated gene YLR087c of strain HL13.2.30 lodged with the CNCM under number I-1841, obtained by direct sequencing is given (SEQ ID No. 1), as well as that of the protein encoded by the latter (SEQ ID No. 2).

5) Reintroduction of a DNA fraament carryina the STOP mutation in a yeast strain and investigation of the phenotype conferred a) Construction of the plasmid pUC$_9$-3162Δ'418

In order to verify that the only STOP mutation identified by the sequencing was necessary and sufficient to confer a phenotype of cold-sensitivity on a yeast, we sub-cloned a fragment of 3162 bp (fragment HindIII, nucleotides 6035–9196 of the mutated gene YLR087c, in sequence SEQ ID No. 1, containing the STOP mutation at position 7865). A marker of geneticin resistance (G418) was then introduced in the single site Eco RV (position 8379 of the gene) to make it possible to select yeasts that have been transformed by this fragment by homologous recombination.

Figure 3:
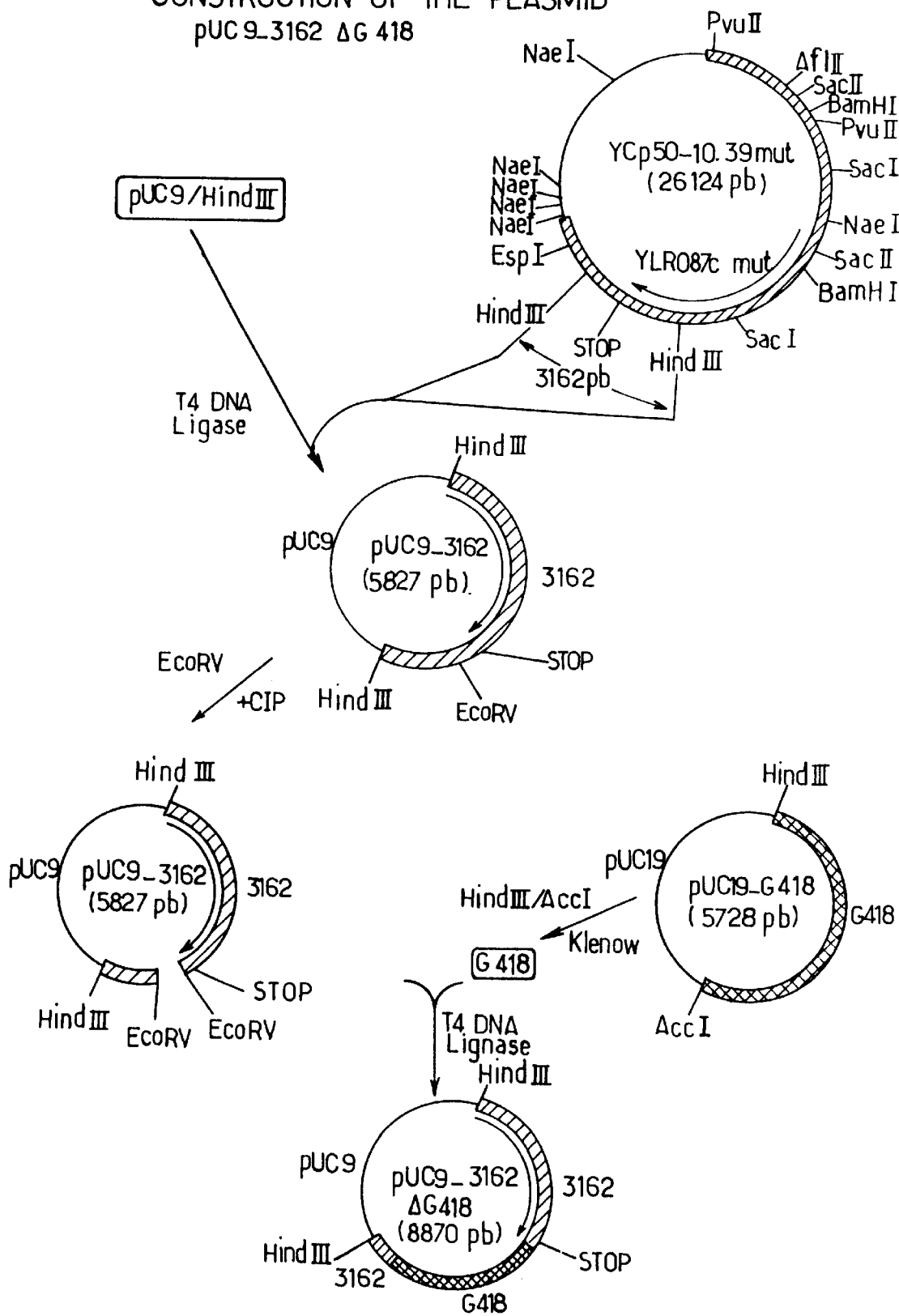
FIG. 3 is a diagrammatic representation of the construction of the plasmid pUC 9_3162 ΔG 418.

The details of the construction are given below (and are explained schematically in FIG. 3):

Isolation of the 3162 bp fragment Hind III by hydrolysis of the plasmid YCp50-10.39mut containing the mutated gene YLR087c. The fragment is separated by electrophoresis on low-melting-point agarose (LMP agarose) and purified by Kit QIAEX QIAGEN).

Cloning of the 3162 bp fragment Hind III described above in plasmid pUC$_9$ at the single site Hind III present in the multiple cloning site of this vector. We then obtain the plasmid designated pUC$_9$-3162.

Opening of plasmid pUC$_9$-3162 at the single site Eco RV contained in the 3162 bp fragment (position No. 8379 of the gene—SEQ ID No. 1). This enzyme (Eco RV) releases flush ends which are then dephosphorylated by the action of CIP (Calf Intestine Phosphatase).

Preparation of the DNA fragment pPGK/Tn903/tPGK corresponding to the geneticin resistance gene (G418) by double hydrolysis Hind III/AccI of plasmid pUC$_{19}$-G418. The 3.1 kb fragment is recovered by electrophoresis on IMP agarose gel followed by purification by kit QIAEX. This fragment is then rendered blunt-ended by the action of DNA polymerase (Klenow fragment) in the presence of the 4 DNTP.

The G418 resistance gene that has been made blunt-ended (see above for description) is then cloned at site Eco RV of plasmid pUC$_9$-3162 by the action of T4 DNA ligase. After transformation of the E. coli strain DH5α, we obtain the plasmid pUC$_9$-3162ΔG418 which carries a DNA fragment of about 6.2 kb containing the STOP mutation and the G418 resistance gene.

b) Transformation of the haploid strains of yeasts M5 and OL1

Hydrolysis of plasmid pUC$_9$-3162ΔG418 makes it possible to liberate a linear DNA fragment of 6.2 kb which can, by homologous recombination, replace the corresponding part of a wild-type gene YLR087c by the same fragment carrying the STOP mutation. Integration is effected by gene replacement, by a mechanism of double crossing-over as described by RODSTEIN, R. (1991) Methods in Enzymology, 194, 281–301. The G418 resistance gene, inserted 514 bp after the STOP mutation (in the 5'→3| direction of reading of the ORF) is only useful for the selection of transformants.

Two independent haploid laboratory strains of Saccharomyces cerevisiae: M5 (MATA, ura3, trp1, leu2) and OL1 (MATα, leu2, his 3, ura3) were transformed with linear DNA 3162ΔG418 (6.2 kb fragment Hind III of plasmid pUC$_9$-3162ΔG418) by electroporation according to the method described by NEILHOC, E. et al. (1990) Biotechnology, 8, 223–227. The electroporation conditions are as follows:

2500 V/cm $10^8$ cells in 50 μl

1 μg of linear DNA.

Several hundred G418-resistant transformant clones were obtained with these two strains. Analysis of 20 clones taken at random for each of these two strains showed that all these clones had a phenotype of cold-sensitivity.

Strain M5 is a true 16n haploid (16 chromosomes) derived from strain M5 2n described by SCHAAFF et al. (1989) Curr.Genet. 15, 75–81. Strain OL1 is a true 16n haploid described by BOY-MARCOTTE, E. and JACQUET, M. (1982) Gene 20, 433–440.

This result shows that when the mutation is reinserted in a haploid yeast strain by the technique of gene replacement, this imparts a phenotype of cold-sensitivity to the transformed clones.

6) Construction of industrial cold-sensitive strains of bread-making yeast by introducing the STOP mutation in all of their YLR087c genes The STOP mutation identified in the YLR087c gene and described above is a recessive mutation, which can be transmitted and is not dependent on a particular genetic context of the strain (cf. transformation of two independent laboratory strains described above in 5).

To construct a cold-sensitive strain of industrial yeast it is necessary to introduce the STOP mutation identified in all the alleles of the YLR087c gene present in the strain to endow it with the phenotype of cold-sensitivity. The constructions described in 5 above (pUC$_9$-3162 and pUC$_9$-3162ΔG418) make it possible to achieve this objective. On the same model of construction of the vector pUC$_9$-3162ΔG418, it is possible to introduce other positive markers, for example the gene for resistance to phleomycin, to cycloheximide, to herbicides, to metals (Cu, Cd). Following the same procedure (gene replacement) as that described above, all the wild-type alleles of the YLR087c gene can be transformed so as to introduce the STOP mutation and a positive marker that is different for each allele of the YLR087c gene. A "clean" strain, containing only the single change of nucleotide 7865 of sequence SEQ ID No. 1 (STOP mutation, position 308242 of chromosome XII of *Saccharomyces cerevisiae* according to the data bank of the MIPS) is then obtained by transforming the strain several times by a technique of co-transformation employing the linear DNA fragment of 3162 bp (obtained by HindIII digestion of plasmid pUC$_9$-3162) and a plasmid of type YEP containing a positive marker other than those used in the transformations by integration. The clones obtained after co-transformation are then replicated in dishes containing a suitable medium, each dish containing one toxic substance (antibiotic, herbicide, etc.) used during the integration stages. The clones that have lost at least one of the resistance characters are selected. At the end of this selection by replicas, the replicative plasmid used during co-transformation is eliminated by cultivating the selected clone or clones on a rich medium without any selection pressure. At the end of this culture, we obtain a clone that has lost the resistance character carried by the plasmid.

Repetition of this sequence of transformation events makes it possible to replace one by one the mutated alleles carrying a resistance marker by alleles carrying the mutation alone without other heterologous DNA of the resistance marker type.

It is preferable to use a strain of baker's yeast possessing a limited number of copies of the YLR087c gene. It is further preferable to transform the parents (segregants) of this strain first, which will be re-crossed once the phenotype of cold-sensitivity has been obtained for each of the parents.

Alternatively, it is possible to make use of the method of selection by enrichment with nystatin described in example 1.

In this case, we again proceed by co-transformation employing the linear DNA carrying the STOP mutation (3162 bp fragment Hind III of plasmid PUC$_9$-3162) and a replicative plasmid of type YEp carrying a positive marker (resistance to G418 or to phleomycin). The antibiotic-resistant clones obtained after co-transformation are collected and submitted to the nystatin enrichment protocol which makes it possible to select cells that have the phenotype of cold-sensitivity. The replicative plasmid carrying a resistance marker is then eliminated by cultivating a clone (selected as cold-sensitive) on rich medium without selection pressure (loss of the plasmid). This alternative permits direct selection of multiple integration events (by gene replacement) that could have occurred. Once again it is preferable to work with a strain possessing a limited number of copies of the YLR087c genes or even better, to transform the parents of this strain beforehand.

The construction can be verified by sequencing a PCR product covering the zone that is the site of the desired genetic manipulation.

A third alternative can also be employed to achieve the desired objective of replacing each YLR087c allele of an industrial strain with alleles carrying the STOP mutation. This method is described in the article published by ALANI, E. et al. (1987) "Genetics" 116, 541–545. It consists of flanking a positive marker, for example the G418 resistance gene, by two direct repeat sequences, preferably sequences identical to the YLR087c gene. Culture of a G418-resistant transformant on a rich medium without G418 permits excision of the marker by a "pop-out" mechanism. Repetition of this sequence of integration/excision makes it possible, as described in the article cited above, for each of the wild-type alleles to be replaced one by one by alleles carrying the STOP mutation.

This example is non-limitative, and one may consider that an identical result can be obtained by non-lethal mutations of other genes comparable to the YLR087c gene coding for membrane proteins, it being understood that each of the genes that are similar or have the same properties as the YLR087c gene can carry the same non-lethal mutation. These genes similar to the YLR087c gene are for example:

genes possessing a comparable function genes coding for proteins associated with the protein coding for the YLR087c gene genes coding for proteins possessing similarities of sequence, i.e. at least 50% homology, preferably at least 60% homology, and more preferably at least 70% homology with the protein encoded by the YLR087c gene.

EXAMPLE 5

Test of Bread-Making with Blocked Rise

Fresh bread-making yeasts obtained in accordance with example 2 with strains S47 and S47-12b1 are tested according to the following recipe and instructions for bread-making:

Recipe:

| | |
|---|---|
| flour | 100 (or 8000 g) |
| water | 61 (or 4880 g) |
| salt | 2.1 (or 168 g) |
| fresh yeast | 3 (or 240 g) |
| Croustiliss$^{(R)}$ détente | 1 (or 80 g) |
| gluten | 1 (or 80 g). |

Croustiliss® détente [expansion] is the trademark of a bread-making improver marketed by the company Lesaffre Ingredients, 26 rue Gabriel Péri, 59700 Marcq-en-Baroeul, France and which supplies mono- and diglycerides of fatty acids (emulsifier E471), deactivated yeasts with reducing power, ascorbic acid and fungal alpha-amylases with secondary effect.

The flour is a flour of type 55 giving, on the Chopin alveograph [for determining bread texture]:

W=256–P=79–L=92–P/L=0.86 and not containing ascorbic acid. These characteristics of flours are defined in the work: "Guide Pratique d'Analyses dans les Industries des Céréales" [Practical guide to analyses in the cereals industries], coordinated by B. GODON and W. LOISEL, Technique et Documentation LAVOISIER, 1984.

Bread-making instructions:

| kneading in KEMPER(R) spiral mixer | 3 minutes at 1st speed + 5 minutes at 2nd speed |
| --- | --- |
| dough temperature | 25° C. |
| rest | 10 minutes |
| division into 350 g lumps | |
| expansion | 15 minutes |
| shaping to beguette shape | |
| finishing at 28° C. at constant volume | about 110 minutes | blocking of the lumps at the end of finishing at 8° C. for 4 hours, 19 hours and 22 hours
baking after blocking at 8° C., bearing in mind that after blocking for 19 hours and 22 hours, a time of reheating of the lumps of one hour at 28° C. is observed.

The mixer used is a KEMPER® mixer of type "Mixhneter Standard" made by EMIL KEMPER GMBH 4835 Rietberg 2—Neueckirchen—Germany.

Results:

The baguettes obtained with the bread-making yeast derived from strain S47 are too developed from 4 hours at 8° C., with indistinct knife cuts. These faults are accentuated after 19 hours and 22 hours. The baguettes obtained with the bread-making yeast derived from strain S47-12b1 are well developed, with well defined knife cuts and a good general appearance after blocking for 4 hours, 19 hours and 22 hours.

EXAMPLE 6

Test of Bread-Making with Slow Rise

The fresh bread-making yeasts obtained according to example 2 with strains S47 and S47-12b1 are tested according to the following bread-making recipe and instructions:

Recipe:

| flour | 100 (or 8000 g) |
| --- | --- |
| water | 61 (or 4880 g) |
| salt | 2.1 (or 168 g) |
| fresh yeast | 1 (or 80 g) |
| Croustiliss(R) slow-rise | 1 (or 80 g) |
| gluten | 0.5 (or 40 g). |

The flour is of the same type as in the preceding example.

Croustiliss® slow-rise is the trademark of a bread-making improver marketed by Lesaffre Ingredients and which supplies mono- and diglycerides of fatty acids, ascorbic acid and fungal alpha-amylases of the optimum quality and dose for processes of the slow-rise type.

Bread-making instructions:

| kneading in KEMPER(R) spiral mixer | 3 minutes at 1st speed + 5 minutes at 2nd speed |
| --- | --- |
| dough temperature | 24° C. |
| rest | 15 minutes |
| division into 350 g lumps | |

| expansion | 15 minutes |
| --- | --- |
| shaping to baguette shape | | finishing from 16 hours to 24 hours at 15° C. then backing.

Results:

The baguettes obtained with the bread-making yeast derived from strain S47 have risen too much at the end of 16 hours, they are too voluminous, and the knife cuts are indistinct. We have already passed or are at the limit of the maximum fermentation time for this yeast.

On the other hand, in the range 16 to 24 hours, with the bread-making yeast obtained with strain S47-12b1 we obtain baguettes with a good general appearance, with well-defined knife cuts. At the end of 16 hours, the baguettes are a little less developed, at the end of 24 hours we obtain baguettes at the upper limit of volume. For 8 hours, with a dough kneaded and shaped the day before, we have lumps that are ready to bake on demand, which give baguettes with a good appearance.

Of course, these examples are not limitative. For example, it is evident that with the novel bread-making yeast obtained with strain S47-12b1 it is possible to combine slow rise and blocked rise so as to extend the cooking range. With it, it is easy to obtain lumps that are ready to bake on demand over long periods of time, at least 4 hours, and preferably at least 8 hours.

EXAMPLE 7

Bread-Making Doughs Fermented in Blocked Mix

The recipe used is a standard recipe for French bread characterized by increased hydration of the dough of at least 4 points, owing to the production scheme with pointing or first fermentation that is long, which gives the dough considerable strength.

This recipe is:

| flour | 100 |
| --- | --- |
| water | 66 |
| salt | 2 |
| fresh yeast | 3 |
| improver | 1 |

The fresh yeasts used are the yeasts obtained according to example 2 with strains S47 (control) and S47-12b1 (strain exhibiting the phenotype of cold-sensitivity in fermentation).

The improver used can be the improver Ibis® blue, or preferably an improver from the Croustiliss® range, improvers that are sold by Lesaffre Ingredients. The longer the dough in bulk is stored, the greater is the need for a Croustiliss® improver, which supplies monoglycerides of fatty acids and is rich in ascorbic acid.

Kneading is effected in a spiral mixer from the company VMI, ZI Nord, F-85601 Montaigu, 4 minutes at first speed, followed by 8 minutes at second speed. The dough obtained is at 24° C.

The lumps obtained in 8 kg vats are placed in a cold chamber at −10° C. until the dough has a core temperature of +4° C., and are then stored at +4° C.

During the time that the temperature falls, there is a first fermentation or pointing.

After 3 days of blocking at 4° C., the dough with the control yeast is too fermented, whereas the dough with the cold-sensitive yeast (strain S47-12b1) is still stable. The control dough is barely tolerant to finishing. After blocking for 7 days, the control dough is no longer usable. In all bread-making, comprising the additional operations of division of the dough, making lumps, shaping of the dough, short finishing, baking, for the 7 days with the dough made with the yeast obtained with strain S47-12b1 we obtain baguettes with excellent traditional organoleptic quality. These additional operations, owing to the use of a fermented dough that has undergone long pointing giving strength and aroma, can be carried out in less than 3 hours, preferably in less than 2 hours. This production scheme using a bread-making yeast obtained with a strain that possesses a phenotype of cold-sensitivity in fermentation has the following advantages:

production of dough in bulk in large quantity which can be stored without any problems for at least 7 days, control of the refrigeration temperature so as to have a first fermentation or pointing giving strength and aroma to the dough, and then preserving its rheological properties for at least 7 days, production of bread of very high organoleptic quality with a short final production scheme with maximum duration of 3 hours and preferably less than 2 hours.

In general, the use of yeasts obtained with a strain that has a phenotype of cold-sensitivity in fermentation makes it possible to obtain doughs in bulk regardless of their composition, which keep well at 4° C. and are easy to transport. These bulk doughs packaged in large containers, for example in buckets, or in vats (which is equivalent to bulk supply) offer considerable advantages with respect to centralization or rearrangement of manufacturing operations, with possibilities of distribution of the dough in bulk to several points of final production. This use of yeasts that have a phenotype of cold-sensitivity is particularly beneficial for preparing doughs that are ready to use or to bake for distribution to various cooking points.

These logistical advantages are generally obtained regardless of the moment when the production process is halted by temperatures below or equal to 10° C.: leaven, bulk fermented dough, shaped dough, ready-to-bake dough.

Moreover, these advantages can be combined with the choice of production processes giving important additional advantages in bread-making:

the use of bread-making doughs for bread of the French type in blocked mix, cooling of which is controlled so as to have a long first fermentation or a long pointing is one example of these advantages. It is then possible for highly aromatic bread of the traditional type to be produced quickly;

control of the composition and of the aromas produced in leavens containing a flora composed of a strain of cold-sensitive yeast and lactic bacteria, preferably psychrophilic, i.e. developing rapidly in the cold, is another example of a novel application that is particularly beneficial in bread-making.

What is claimed is:

1. A *Saccharomyces cerevisiae* strain giving way of cultivation fresh bread-making yeasts providing a release of at least 100 ml of $CO_2$ in 2 hours at 30° C. in test $A_1$ and a release of $CO_2$ in 48 hours at 8° C. in test $A_1$ such that the ratio:

$$\frac{\text{release of } CO_2 \text{ in 48 hours at 8° C. in test } A_1}{\text{release of } CO_2 \text{ in 2 hours at 30° C. in test } A_1} \text{ is less than 45\%,}$$

wherein test $A_1$ comprises
- adding to 20 g of flour incubated at the temperature selected for the measurement of release of $CO_2$, an amount of compressed yeast corresponding to 160 mg of dry matter,
- diluting said yeast in 15 ml of water containing 27 g NaCl per liter and 4 g of $(NH_4)_2SO_4$ per liter,
- mixing with a spatula for 40 seconds in order to obtain a dough,
- placing said dough in a vessel containing a water bath whose temperature is set to the abovesaid temperature,
- sealing hermetically said vessel containing the dough thirteen minutes after the start of mixing, and
- measuring the total quantity of gas produced after 60, then 120 minutes or several hours, said quantity being expressed in ml at 20° C. and at 760 mm Hg.

2. A *Saccharomyces cerevisiae* strain according to claim 1, wherein the fresh bread-making yeast obtained by way of cultivation of said strain provides a release of $CO_2$ in 2 hours at 30° C. in test $A_1$ of at least 110 ml and a release of $CO_2$ in 48 hours at 8° C. in test $A_1$ such that the ratio:

$$\frac{\text{release of } CO_2 \text{ in 48 hours at 8° C. in test } A_1}{\text{release of } CO_2 \text{ in 2 hours at 30° C. in test } A_1} \text{ is less than 40\%.}$$

3. A *Saccharomyces cerevisiae* strain according to claim 1, wherein the fresh bread-making yeast obtained by way of cultivation of said strain provides a release of $CO_2$ in 2 hours at 30° C. in test $A_1$ of at least 150 ml and a release of $CO_2$ in 48 hours at 8° C. in test $A_1$ such that the ratio:

$$\frac{\text{release of } CO_2 \text{ in 48 hours at 8° C. in test } A_1}{\text{release of } CO_2 \text{ in 2 hours at 30° C. in test } A_1} \text{ is less than 45\%.}$$

4. A *Saccharomyces cerevisiae* strain according to claim 1, wherein the fresh bread-making yeast obtained by way of cultivation of said strain provides a release of $CO_2$ in 2 hours at 30° C. in test $A_1$ of at least 100 ml and a release of $CO_2$ in 48 hours at 8° C. in test $A_1$ such that the ratio:

$$\frac{\text{release of } CO_2 \text{ in 48 hours at 8° C. in test } A_1}{\text{release of } CO_2 \text{ in 2 hours at 30° C. in the } A_1} \text{ is less than 30\%.}$$

5. A *Saccharomyces cerevisiae* strain having a phenotype of cold sensitivity which is the same as the phenotype of the strains according to claim 1, said strain being obtained by selecting a rapid industrial *Saccharomyces cerevisiae* strain well adapted to maltose or the haploids used for its construction and by subjecting said strain to a recombinant site-directed mutagenesis which consists of specifically reproducing in the said strain or in the corresponding starting haploids at least one mutation providing the selected strain with the requested phenotype.

6. A *Saccharomyces cerevisiae* strain according to claim 5, comprising a non-lethal mutation on its YLR087c genes, wherein the mutation is a change causing the appearance of a stop codon, in position 7865 in sequence SEQ ID No. 1, corresponding to position No. 308242 in chromosome XII in the sequence of the data bank of the Martinsried Institute for Protein Sequences.

7. A method for obtaining acid leavens or sour doughs comprising yeast and lactic bacteria, said method comprising the step of inoculating said leavens or sour doughs with a strain having the phenotype of the *Saccharomyces cerevisiae* strain according to claim 1.

8. A method of making frozen doughs wherein the dough issued from the kneading step contains a fresh or dry yeast obtained by cultivating a *Saccharomyces cerevisiae* strain according to claim 1.

9. A method for producing doughs in bulk comprising incorporating into a dough fresh or dry yeasts obtained by cultivating a *Saccharomyces cerevisiae* strain according to claim 1.

10. A deferred bakery method comprising a kneading step for the preparation of a dough and a baking step, said kneading and baking steps being separated by a period of more than 6 hours wherein said dough contains fresh or dry yeast obtained by cultivating a *Saccharomyces cerevisiae* strain according to claim 1, said method providing lumps of dough that remain ready to bake for a period of at least 8 hours.

11. A deferred bakery method comprising a kneading step for the preparation of a dough and a baking step, said kneading and baking steps being separated by a period of more than 6 hours wherein said dough contains a fresh or dry yeast obtained by cultivating a *Saccharomyces cerevisiae* strain according to claim 1, said method providing bread of the French type.

12. The method according to claim 9 wherein said pre-fermented doughs are leavens, flour brews, or sponges.

13. A method according to claim 9 wherein the bulk dough is selected from the group consisting of prefermented doughs and first fermentation doughs.

14. A method according to claim 9 wherein the bulk doughs are doughs that are ready to use or ready to bake for distribution to various baking points.

15. A method for the production of aromatic baking products comprising the steps of preparing fermented bulk doughs with a long first fermentation time, division, shaping, short finishing fermentation time or proofing time and baking wherein the fermented bulk doughs contain a fresh or dry yeast obtained by cultivating a *Saccharomyces cerevisiae* strain according to claim 1.

16. Strain S47-12b1 deposited with the National Centre for Culture of Microorganisms (CNCM) under No. I-1645.

17. Strain L30-13 deposited with the National Centre for Culture of Microorganisms (CNCM) under No. I-1647.

18. Strain L30-91 deposited with the National Centre for Culture of Microorganisms (CNCM) under No. I-1646.

19. Strain HL13.2.30 deposited with the National Centre for Culture of Microorganisms (CNCM) under No. I-1841.

20. A method for obtaining acid leavens or sour doughs comprising yeast and lactic bacteria, said method comprising the step of inoculating said leavens or sour doughs with a strain having the phenotype of the *Saccharomyces cerevisiae* strain according to claim 16.

21. A method for obtaining acid leavens or sour doughs comprising yeast and lactic bacteria, said method comprising the step of inoculating said leavens or sour doughs with a strain having the phenotype of the *Saccharomyces cerevisiae* strain according to claim 17.

22. A method for obtaining acid leavens or sour doughs comprising yeast and lactic bacteria, said method comprising the step of inoculating said leavens or sour doughs with a strain having the phenotype of the *Saccharomyces cerevisiae* strain according to claim 18.

23. A method for obtaining acid leavens or sour doughs comprising yeast and lactic bacteria, said method comprising the step of inoculating said leavens or sour doughs with a strain having the phenotype of the *Saccharomyces cerevisiae* strain according to claim 19.

24. A *Saccharomyces cerevisiae* strain having a phenotype of cold sensitivity which is the same as the phenotype of a strain selected from the group consisting of the strains according to one of claims 16, 17, 18, 19 or 1, said strain being obtained by a process implementing the techniques of molecular biology and comprising:

selecting one or more genes which have an action of the fermentation of sugars, transforming a *Saccharomyces cerevisiae* strain in order that the said gene(s) has (have) a conditional expression which depends on the temperature.

25. A method of making frozen doughs wherein the dough issued from the kneading step contains a fresh or dry yeast obtained by cultivating a *Saccharomyces cerevisiae* strain according to claim 16.

26. A method of making frozen doughs wherein the dough issued from the kneading step contains a fresh or dry yeast obtained by cultivating a *Saccharomyces cerevisiae* strain according to claim 17.

27. A method of making frozen doughs wherein the dough issued from the kneading step contains a fresh or dry yeast obtained by cultivating a *Saccharomyces cerevisiae* strain according to claim 18.

28. A method of making frozen doughs wherein the dough issued from the kneading step contains a fresh or dry yeast obtained by cultivating a *Saccharomyces cerevisiae* strain according to claim 19.

29. A deferred bakery method comprising a kneading step for the preparation of a dough and a baking step, said kneading and baking steps being separated by a period of more than 6 hours wherein said dough contains a fresh or dry yeast obtained by cultivating a *Saccharomyces cerevisiae* strain selected from the group consisting of the strains according to one of claims 16, 17, 18, 19 or 1.

30. A deferred bakery method comprising a kneading step for the preparation of a dough and a baking step, said kneading and baking steps being separated by a period of more than 6 hours wherein said dough contains a fresh or dry yeast obtained by cultivating a *Saccharomyces cerevisiae* strain selected from the group consisting of the strains according to one of claims 16, 17, 18, 19 or 1, said method providing lumps of dough that remain ready to bake for a period of at least 4 hours.

31. A deferred bakery method comprising a kneading step for the preparation of a dough and a baking step, said kneading and baking steps being separated by a period of more than 6 hours wherein said dough contains fresh or dry yeast obtained by cultivating a *Saccharomyces cerevisiae* strain according to claim 16, said method providing lumps of dough that remain ready to bake for a period of at least 8 hours.

32. A deferred bakery method comprising a kneading step for the preparation of a dough and a baking step, said kneading and baking steps being separated by a period of more than 6 hours wherein said dough contains a fresh or dry yeast obtained by cultivating a *Saccharomyces cerevisiae* strain according to claim 17, said method providing lumps of dough that remain ready to bake for a period of at least 8 hours.

33. A deferred bakery method comprising a kneading step for the preparation of a dough and a baking step, said kneading and baking steps being separated by a period of more than 6 hours wherein said dough contains a fresh or dry yeast obtained by cultivating a *Saccharomyces cerevisiae* strain according to claim 18, said method providing lumps of dough that remain ready to bake for a period of at least 8 hours.

34. A deferred bakery method comprising a kneading step for the preparation of a dough and a baking step, said kneading and baking steps being separated by a period of more than 6 hours wherein said dough contains a fresh or dry yeast obtained by cultivating a *Saccharomyces cerevisiae* strain according to claim 19, said method providing lumps of dough that remain ready to bake for a period of at least 8 hours.

35. A deferred bakery method comprising a kneading step for the preparation of a dough and a baking step, said kneading and baking steps being separated by a period of more than 6 hours wherein said dough contains a fresh or dry yeast obtained by cultivating a *Saccharomyces cerevisiae* strain according to claim 16, said method providing bread of the French type.

36. A deferred bakery method comprising a kneading step for the preparation of a dough and a baking step, said kneading and baking steps being separated by a period of more than 6 hours wherein said dough contains a fresh or dry yeast obtained by cultivating a *Saccharomyces cerevisiae* strain according to claim 17, said method providing bread of the French type.

37. A deferred bakery method comprising a kneading step for the preparation of a dough and a baking step, said kneading and baking steps being separated by a period of more than 6 hours wherein said dough contains a fresh or dry yeast obtained by cultivating a *Saccharomyces cerevisiae* strain according to claim 18, said method providing bread of the French type.

38. A deferred bakery method comprising a kneading step for the preparation of a dough and a baking step, said kneading and baking steps being separated by a period of more than 6 hours wherein said dough contains a fresh or dry yeast obtained by cultivating a *Saccharomyces cerevisiae* strain according to claim 19, said method providing bread of the French type.

39. A method for producing doughs in bulk comprising the usual steps among which the preparation of a dough wherein said dough contains a fresh or dry yeast obtained by cultivating a *Saccharomyces cerevisiae* strain according to claim 16.

40. A method for producing doughs in bulk comprising the usual steps among which the preparation of a dough wherein said dough contains a fresh or dry yeast obtained by cultivating a *Saccharomyces cerevisiae* strain according to claim 17.

41. A method for producing doughs in bulk comprising the usual steps among which the preparation of a dough wherein said dough contains a fresh or dry yeast obtained by cultivating a *Saccharomyces cerevisiae* strain according to claim 18.

42. A method for producing doughs in bulk comprising the usual steps among which the preparation of a dough wherein said dough contains a fresh or dry yeast obtained by cultvatng a *Saccharomyces cerevisiae* strain according to claim 19.

43. A method for the production of aromatic baking products comprising the steps of preparing fermented bulk doughs with a long first fermentation time, division, shaping, short finishing fermentation time or proofing time and baking wherein the fermented bulk doughs contain a fresh or dry yeast obtained by cultivating a *Saccharomyces cerevisiae* strain according to claim 16.

44. A method for the production of aromatic baking products comprising the steps of preparing fermented bulk doughs with a long first fermentation time, division, shaping, short finishing fermentation time or proofing time and baking wherein the fermented bulk doughs contain a fresh or dry yeast obtained by cultivating a *Saccharomyces cerevisiae* strain according to claim 17.

45. A method for the production of aromatic baking products comprising the steps of preparing fermented bulk doughs with a long first fermentation time, division, shaping, short finishing fermentation time or proofing time and baking wherein the fermented bulk doughs contain a fresh or dry yeast obtained by cultivating a *Saccharomyces cerevisiae* strain according to claim 18.

46. A method for the production of aromatic baking products comprising the steps of preparing fermented bulk doughs with a long first fermentation time, division, shaping, short finishing fermentation time or proofing time and baking wherein the fermented bulk doughs contain a fresh or dry yeast obtained by cultivating a *Saccharomyces cerevisiae* strain according to claim 19.

* * * * *